United States Patent
Sharpe et al.

(10) Patent No.: US 11,591,566 B2
(45) Date of Patent: Feb. 28, 2023

(54) METHODS FOR HIGH THROUGHPUT SPERM SORTING

(71) Applicant: INGURAN, LLC, Navasota, TX (US)

(72) Inventors: Johnathan Charles Sharpe, Hamilton (NZ); Nemanya Sedoglavich, Boston, MA (US); Blair Morad, Belmont, MA (US); Donald Francis Perrault, Jr., Brighton, MA (US)

(73) Assignee: Inguran, LLC, Navasota, TX (US)

( * ) Notice: Subject to any disclaimer, the term of this patent is extended or adjusted under 35 U.S.C. 154(b) by 636 days.

(21) Appl. No.: 16/577,872

(22) Filed: Sep. 20, 2019

(65) Prior Publication Data

US 2020/0017826 A1 Jan. 16, 2020

Related U.S. Application Data

(63) Continuation of application No. 13/830,365, filed on Mar. 14, 2013, now Pat. No. 10,662,408.

(51) Int. Cl.
*G01N 15/14* (2006.01)
*C12N 5/071* (2010.01)

(52) U.S. Cl.
CPC ....... *C12N 5/0612* (2013.01); *G01N 15/1459* (2013.01); *G01N 15/1484* (2013.01); *G01N 2015/149* (2013.01)

(58) Field of Classification Search
CPC .............. C12N 5/0612; G01N 15/1459; G01N 2015/149; G01N 2015/1413
See application file for complete search history.

(56) References Cited

U.S. PATENT DOCUMENTS

| | | | |
|---|---|---|---|
| 4,756,427 A | 7/1988 | Gohde et al. | |
| 4,983,038 A | 1/1991 | Ohki et al. | |
| 5,007,732 A | 4/1991 | Ohki et al. | |
| 5,135,759 A | 8/1992 | Johnson | |
| RE35,227 E | 5/1996 | Tomioka et al. | |
| 5,608,519 A | 3/1997 | Gourley et al. | |
| 5,690,895 A | 11/1997 | Matsumoto et al. | |
| 5,726,751 A | 3/1998 | Altendorf | |
| 5,779,976 A | 7/1998 | Leland et al. | |
| 5,858,187 A | 1/1999 | Ramsey et al. | |
| 5,985,216 A | 11/1999 | Rens et al. | |

(Continued)

FOREIGN PATENT DOCUMENTS

| | | |
|---|---|---|
| JP | 05322740 A | 12/1993 |
| JP | 10-0279908 A | 12/2010 |

(Continued)

OTHER PUBLICATIONS

International Search Report and Written Opinion dated May 23, 2013 in corresponding PCT Application No. PCT/US13/31706.

(Continued)

*Primary Examiner* — Howard J Sanders
*Assistant Examiner* — Jessica L Burkman
(74) *Attorney, Agent, or Firm* — Ryan Christensen; Hashim Rahman

(57) ABSTRACT

This disclosure relates to methods for sorting sperm cells in a microfluidic chip. In particular, various steps are incorporated to align and orienting sperm in flow channels, as well as, to determining sperm orientation and measure relative DNA content for analysis and/or sorting.

27 Claims, 27 Drawing Sheets

(56) References Cited

U.S. PATENT DOCUMENTS

| | | | |
|---|---|---|---|
| 6,159,739 | A | 12/2000 | Weigl |
| 6,357,307 | B2 | 3/2002 | Buchanan et al. |
| 6,497,252 | B1 | 12/2002 | Kohler et al. |
| 6,506,609 | B1 | 1/2003 | Wada et al. |
| 6,696,022 | B1* | 2/2004 | Chan ............... B01F 25/432 422/68.1 |
| 6,877,528 | B2 | 4/2005 | Gilbert et al. |
| 7,069,943 | B2 | 7/2006 | Gilbert et al. |
| 7,105,355 | B2 | 9/2006 | Kurabayashi et al. |
| 7,311,476 | B2 | 12/2007 | Gilbert et al. |
| 7,492,522 | B2 | 2/2009 | Gilbert et al. |
| 7,569,788 | B2 | 8/2009 | Deshpande et al. |
| 7,638,339 | B2 | 12/2009 | Sundararajan et al. |
| 7,758,811 | B2 | 7/2010 | Durack |
| 8,123,044 | B2 | 2/2012 | Johnson et al. |
| 8,186,913 | B2 | 5/2012 | Toner et al. |
| 8,198,093 | B2 | 6/2012 | Durack et al. |
| 8,277,764 | B2 | 10/2012 | Gilbert et al. |
| 8,933,395 | B2 | 1/2015 | Mueth et al. |
| 9,464,977 | B2* | 10/2016 | Di Carlo ............ G01N 15/1484 |
| 2003/0054558 | A1 | 3/2003 | Kurabayashi et al. |
| 2004/0011975 | A1 | 1/2004 | Nicoli et al. |
| 2004/0043506 | A1 | 3/2004 | Haussecker |
| 2005/0123451 | A1 | 6/2005 | Nomura |
| 2006/0278288 | A1 | 12/2006 | Gilbert |
| 2008/0213821 | A1 | 9/2008 | Liu et al. |
| 2008/0233635 | A1 | 9/2008 | Evans |
| 2008/0261295 | A1 | 10/2008 | Butler et al. |
| 2008/0272034 | A1 | 11/2008 | Ferren et al. |
| 2009/0011430 | A1 | 1/2009 | Ateya et al. |
| 2009/0023132 | A1 | 1/2009 | Champseix |
| 2009/0066315 | A1 | 3/2009 | Hu et al. |
| 2010/0111616 | A1 | 5/2010 | Gilbert et al. |
| 2011/0008767 | A1 | 1/2011 | Durack |
| 2011/0033922 | A1 | 2/2011 | Landers |
| 2011/0134426 | A1 | 6/2011 | Kaduckak et al. |
| 2011/0143389 | A1 | 6/2011 | Sharpe |
| 2011/0181870 | A1 | 7/2011 | Penney et al. |
| 2011/0271746 | A1* | 11/2011 | Shinoda ............ B01L 3/0268 73/61.71 |
| 2012/0122084 | A1 | 5/2012 | Wagner et al. |
| 2012/0138152 | A1 | 6/2012 | Villarruel |
| 2012/0138513 | A1 | 6/2012 | Johnson |
| 2012/0200857 | A1 | 8/2012 | Sharpe et al. |
| 2012/0202237 | A1 | 8/2012 | Sedoglavich |
| 2012/0277902 | A1 | 11/2012 | Sharpe et al. |
| 2012/0307244 | A1 | 12/2012 | Sharpe et al. |
| 2014/0273179 | A1 | 9/2014 | Sharpe |
| 2014/0273192 | A1 | 9/2014 | Sharpe |
| 2014/0367315 | A1 | 12/2014 | Gluckstad |
| 2015/0268244 | A1 | 9/2015 | Cho et al. |

FOREIGN PATENT DOCUMENTS

| | | |
|---|---|---|
| RU | 2408004 C2 | 12/2010 |
| WO | 9810267 A1 | 3/1998 |
| WO | 2001088087 A2 | 11/2001 |
| WO | 2004022147 A1 | 3/2005 |
| WO | 2005075629 A1 | 8/2005 |
| WO | 2006031299 A2 | 3/2006 |
| WO | 2008125081 A1 | 10/2008 |
| WO | 2011/097032 A1 | 8/2011 |
| WO | 2012162181 A1 | 11/2012 |

OTHER PUBLICATIONS

Australian first Office Action dated Jan. 10, 2014, issued in corresponding AU Application No. 2013202635 (5 pp).
Australian Examination report dated Apr. 8, 2014, issued in corresponding AU Application No. 2013202632 (8 pp).
Faivre, M., et al., "Geometrical focusing of cells in a microfluidic device: An approach to separate blood plasma" Biorheology, 2006, vol. 43, pp. 147-159.
Australian Examination Report dated Sep. 17, 2014. issued in related AU Application No. 2013202632 {6 pp).
Australian Examination Report dated Sep. 17, 2014. issued in related AU Application No. 2013202635 {6 pp).
U.S. Office Action dated Oct. 27, 2104, issued in corresponding U.S. Appl. No. 13/830,333 {42 pp).
Mexican Office Action dated Mar. 18, 2020 in related MX Appl. No. MX/A/2015/012550.
Australian Notice of Acceptance dated Sep. 20, 2017 issued in AU Appl. No. 2015203738.
Canadian Notice of Allowance dated Jan. 29, 2018 issued in related CA Appl. No. 2,898,740.
Japanese Notice of Allowance dated Mar. 31, 2018 issued in related JP Appl. No. 2015-561313.
U.S. Office Action dated Mar. 14, 2018 issued in related U.S. Appl. No. 13/830,333.
Korean Notification of Ground for Rejection dated Mar. 21, 2018 issued in related KR Appl. No. 9-5-2018-019897975.
U.S. Office Action dated Sep. 28, 2018 issued in related U.S. Appl. No. 13/830,333.
Japanese Office Action dated May 28, 2019 issued in related JP Appl. No. 2018-067013.
U.S. Office Action dated Aug. 11, 2019 issued in related U.S. Appl. No. 13/830,365.
U.S. Office Action dated Feb. 24, 2016 issued in related U.S. Appl. No. 13/830,365.
U.S. Office Action dated Jul. 27, 2017 issued in related U.S. Appl. No. 13/830,365.
U.S. Office Action dated Nov. 2, 2017 issued in related U.S. Appl. No. 13/830,365.
U.S. Office Action dated Mar. 7, 2019 issued in related U.S. Appl. No. 13/830,365.
U.S. Notice of Allowance dated Sep. 5, 2019 issued in related U.S. Appl. No. 13/830,365.
Brazilian Examination Report dated Oct. 22, 2019 issued in related BR Appl. No. 112015023155-1.
AU Examination Report dated Feb. 11, 2015 in related Australian Application No. 2013202635.
U.S. Office Action dated Aug. 14, 2015 cited in related U.S. Appl. No. 13/830,333.
Australian Office Action dated Aug. 10, 2015 cited in related AU Appl. No. 2013202635.
U.S. Office Action dated Jul. 8, 2015 cited in related U.S. Appl. No. 13/830,316.
AU Notice of Acceptance dated Oct. 16, 2015 in related AU Application No. 2013202635.
AU Delegate Decision dated Sep. 30, 2015 in related AU Application No. 2013202635.
U.S. Office Action dated Dec. 9, 2015 for U.S. Appl. No. 13/830,333.
U.S. Office Action dated Dec. 22, 2015 for U.S. Appl. No. 13/830,316.
Singapore Office Action dated Feb. 17, 2016 issued in SG Appl. No. 11201505776Y.
Chinese Office Action dated May 24, 17, 2016 issued in CN Appl. No. 201380074401.5.
Japanese Office Action dated Jul. 12, 2016 issued in JP Appl. No. 2015-561313.
U.S. Office Action dated Aug. 26, 2016 issued in U.S. Appl. No. 13/830,333.
Canadian Office Action dated Sep. 13, 2016 issued in CA Appl. No. 2,898,740.
Australian Examination Report dated Oct. 4, 2016 issued in AU Appl. No. 2015203738.
European Search Report dated Oct. 13, 2016 issued in EP Appl. No. 13878058.0.
U.S. Notice of Allowance dated Dec. 27, 2016 issued in U.S. Appl. No. 13/830,316.
Chinese Office Action dated Dec. 14, 2016 issued in CN Appl. No. 201380074.
U.S. Office Action dated Jul. 22, 2016 issued in U.S. Appl. No. 13/830,316.
U.S. Office Action dated Feb. 6, 2016 issued in U.S. Appl. No. 13/830,333.

(56) References Cited

OTHER PUBLICATIONS

New Zealand Examination Report dated Dec. 23, 2016 issued in NZ 630559.
Russian Office Action dated Jan. 9, 2016 issued in RU Appl. No. 2015144002.
Russian Decision to Grant dated Apr. 5, 2017 issued in RU Appl. No. 2015144002.
Japanese Office Action dated Apr. 3, 2016 issued in JP Appl. No. 2015-561313.
U.S. Supplemental Notice of Allowability dated May 3, 2017 issued in U.S. Appl. No. 13/830,316.
Canadian Office Action dated Apr. 18, 2017 issued in CA Appl. No. 2,898,740.
Chinese Office Action dated Apr. 24, 2017 issued in CN Appl. No. 201380074401.5.
Chinese Notice of Allowance dated Jun. 28, 2017 issued in CN Appl. No. 201380074401.5.
U.S. Office Action dated Sep. 19, 2017 issued in U.S. Appl. No. 13/830,333.
New Zealand Examination Report dated Jul. 19, 2017 issued in NZ Appl. No. 630559.
Piyasena, M., et al., "Multinode Acoustic Focusing for Parallel Flow Cytometry", Analytical Chemistry, 2012, vol. 84, pp. 1831-1839.
Johnson, L.A., et al., "Modification of a laser—based flow cytometer for high—resolution DNA analysis of mammalian spermatozoa." Cytometry 7.3 (1986): 268-273.
Johnson, Lawrence A., "Sex preselection by flow cytometric separation of X and Y chromosome-bearing sperm based on DNA difference: a review." Reproduction, Fertility and Development 7.4 {1995): 893-903.
Kachel et al. "Uniform Lateral Orientation, Caused by Flow Forces, of Flat Particles in Flow-Through Systems." vol. 25, No. 7, pp. 774-780, 1977.
Yi, et al. "Microfluidics Technology for Manipulation and Analysis of Biological Cells." Analytica Chimica Acta 560 (2006) 1-23.
Taylor, Jay Kendall. "The Design and Evaluation of a Microfluidic Cell Sorting Chip." A thesis presented to the 1 University of Waterioo in fulfillment of the thesis requirement for the degree of Master of Applied Science in Mechanical Engineering Waterloo, Ontario, Canada, 2007.
Third party submission filed on Oct. 14, 2015 in U.S. Appl. No. 13/830,316.
Scott et CL, Three-dimensional hydrodynamic focusing in a microfluidic Coulter counter, Reviewof Scientific nstruments, 79:046104-1-046104-3 (2008).
Frankowski et al., A Microflow Cytometer Exploited for the Immunological Differentiation of Leukocytes—Cytometry Part A, 79A:613-624 (2011).

Chiu et al., "Universally applicable three-dimensional hydrodynamic microfluidic flow focusing", Lab Chip, 13:1803 2013).
Wolff et al., "Integrating advanced functionality in a microfabricated high-throughput fluorescent-activated cell sorter." cab Chip, 3:22-27 (2003).
Nieuwenhuis et al., "Integrated flow-cells for novel adjustable sheath flows", Lab Chip, 3:56-61 (2003).
Columbian Office Action dated Jun. 2, 2017 issued in CO Appl. No. 2,898,740.
Miyake et al., "A Development of Micro Sheath Flow Chamber," in Proceedings of the IEEE Micro Electro Mechanical Systems Workshop 1991, 265-270 (Jan. 1991).
Tashiro et al., "Design and Simulation of Particles and Biomolecules Handling Micro Flow Cells with Three-Dimensional Sheath Flow," in Proceedings of the µTAS 2000 Symposium, 209-212 (May 14, 2000).
Nieuwenhuis et al., "Particle-Shape Sensing-Elements for Integrated Flow Cytometer," in Proceedings of the µTAS J001 Symposium, 357-358 (Oct. 21, 2001).
Nieuwenhuis et al. "Virtual Flow Channel: A Novel Micro-fluidics System with Orthogonal, Dynamic Control of Sample Flow Dimensions," in Proceedings of the µTAS 2002 Symposium, vol. 1, 103-105 (Nov. 3, 2002).
Dinkel & Stovel, "Flow Chambers and Sample Handling," in Flow Cytometry: Instrumentation and Data Analysis, 91-99 Van Dilla et al., eds.) (1985).
Weigl et al., "Design and Rapid Prototyping of Thin-Film Laminate-Based Microfluidic," Biomedical Microdevices 3 (4):267-274 (2001).
Altendorf et al., "Results Obtained Using a Prototype Microfluidics-Based Hematology Analyzer," in Proceedings of the uTAS 1998 Symposium, 73-76 (Oct. 1998).
Shapiro, Practical Flow Cytometry, 15-17, 133-135 (3d ed. 1995).
Di Carlo et al., "Enhanced Velocity Gradients Within Microfluidics For Cellular Manipulation," in Proceedings of the uTAS 2002 Symposium, vol. 2, 799-801.
Columbian Examination Report dated Dec. 7, 2017 issued in related CO Appl. No. 15234050.
Mexican Office Action dated Mar. 28, 2019 issued in related MX Appl. No. MX/a/2015/012550.
Mexican Office Action dated Jul. 23, 2019 issued in related MX Appl. No. MX/a/2015/012550.
Indian Office Action dated Aug. 13, 2019 issued in related IN Appl. No. 2537/KOLNP/2015.
Russian Office Action dated Jan. 31, 2020 issued in related RU Appl. No. 2017125455.
European Office Action dated Jan. 21, 2020 issued in related EP Appl. No. 13878058.0.

\* cited by examiner

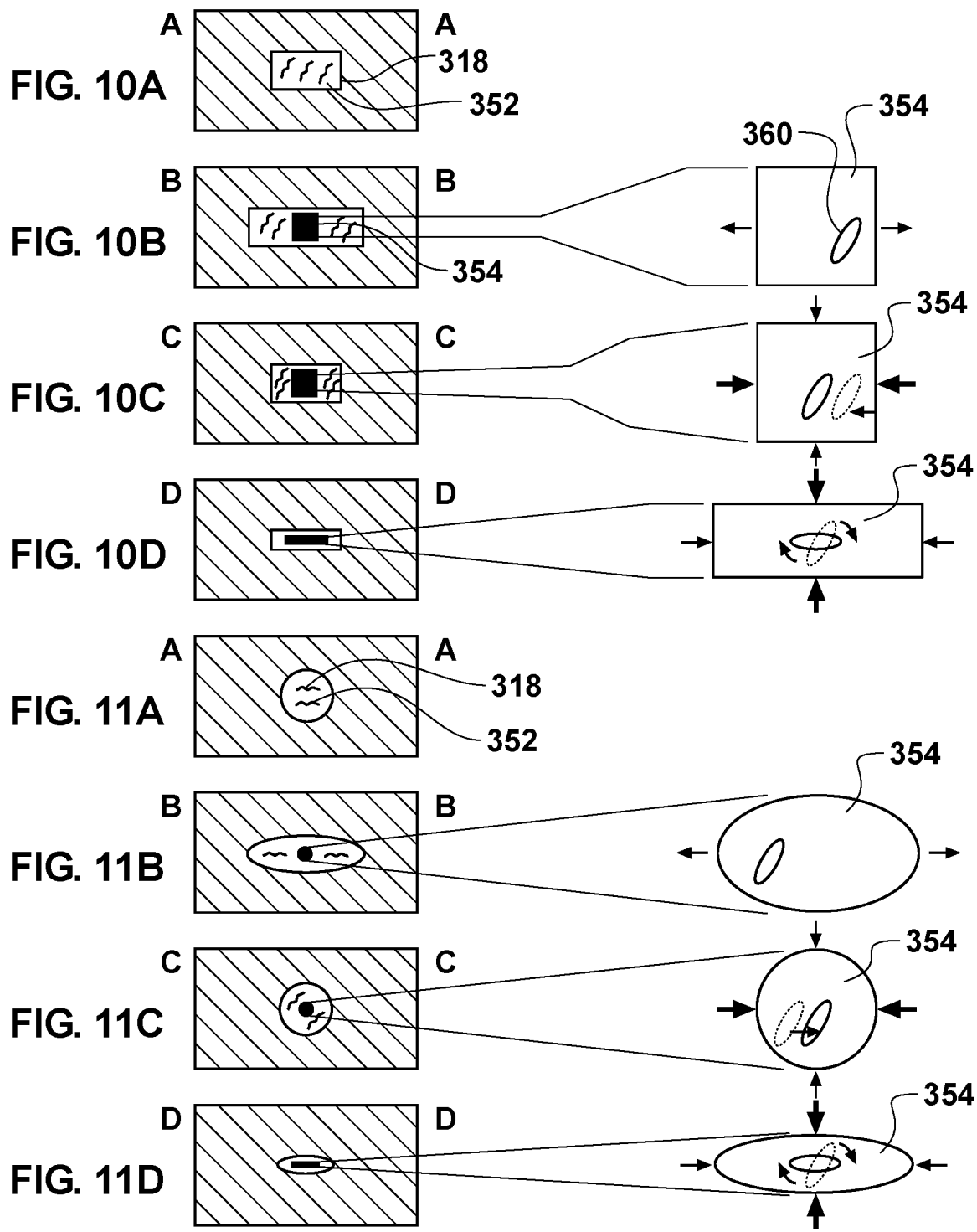

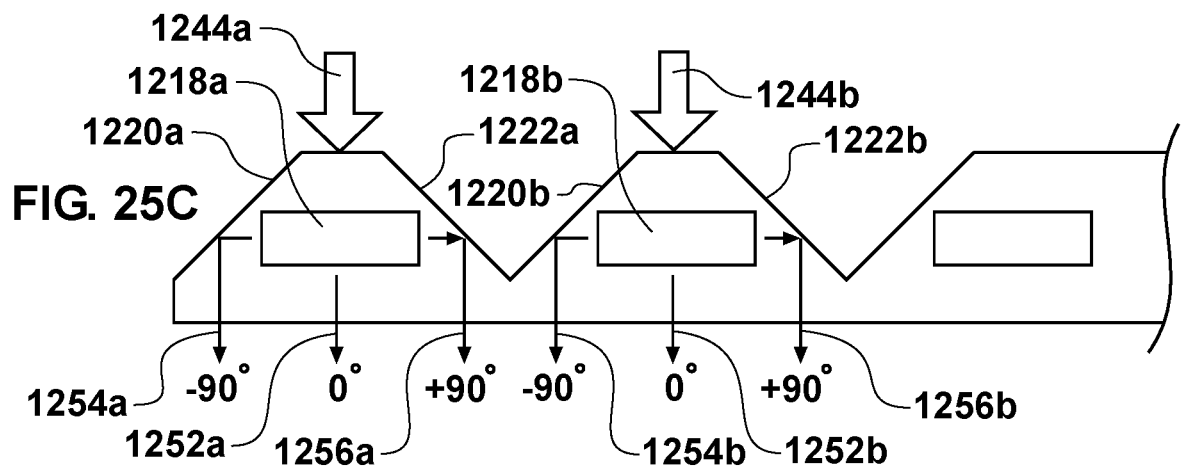
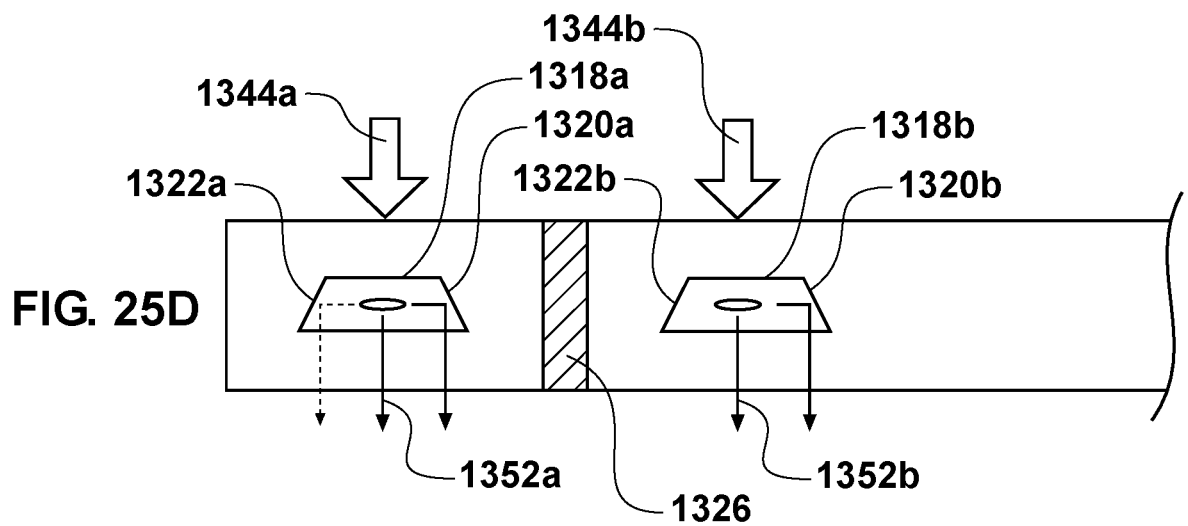

METHODS FOR HIGH THROUGHPUT SPERM SORTING

REFERENCE TO RELATED APPLICATIONS

This application is a continuation of U.S. Utility patent application Ser. No. 13/830,365 filed Mar. 14, 2013, which is incorporated herein by reference in its entirety.

FIELD OF THE INVENTION

Generally, this disclosure relates to a method for sorting particles, and more particularly, relates to the high throughput sorting methods for sperm in a microfluidic chip.

BACKGROUND

Various techniques, including flow cytometry, have been employed to yield sperm populations enriched with respect to certain desired characteristics. In the livestock production industry, an ability to influence reproductive outcomes has obvious advantages. For example, gender pre-selection provides an economic benefit to the dairy industry in that pre-selecting female offspring ensures the birth of dairy cows. Similarly, the beef industry, as well as the pork industry, and other meat producers benefit from the production of males. Additionally, endangered or exotic species can be placed on accelerated breeding programs with an increased percentage of female offspring.

Previous efforts to produce commercially viable populations of sperm sorted for X-chromosome bearing sperm or Y-chromosome bearing sperm largely relied on droplet sorting in jet-in-air flow cytometers. (See e.g. U.S. Pat. Nos. 6,357,307; 5,985,216; and 5,135,759). However, certain drawbacks exist with these methods and devices. Even with advances in droplet flow cytometry, practical limitations still exist which hinder the number of sperm cells that can be sorted in a particular window. As such, sex-sorted artificial insemination (AI) doses are generally smaller than conventional AI doses. In bovine, for example, conventional AI doses may contain about 10 million sperm, whereas sex-sorted doses often contain about 2 million sperm. Conventional AI doses for equine and porcine are in the magnitude of hundreds of millions and billions of spermatozoa, respectively. Sex-sorted sperm, while potentially valuable, has not found widespread use in either species, because lower AI dosages generally result in lower pregnancy and birth rates. Given the large numbers of sperm required in equine and porcine, acceptable dosages have not been achieved for AI.

Sperm are time sensitive and delicate cells that lack the ability to regenerate. Accordingly, longer sorting times are injurious to sperm, as they continuously deteriorate during staining and sorting. Additionally, sperm sorted in a jet-in-air flow cytometer may be subjected to mechanical forces, torsion, stresses, strains and high powered lasers that further injure sperm. Sperm travel at velocities between about 15 m/s and about 20 m/s in the fluid stream of a jet-in-air flow cytometer. These velocities combined with the narrow stream dimensions may give rise to damaging sheering forces that can harm sperm membranes. Additionally, a high laser power is required, as sperm traveling at high velocities remain incident to the beam profile for a shorter period of time providing less of an excitation and measurement window for differentiating sperm. Finally, sperm which is ejected from a jet-in-air nozzle at 15 m/s will impact fluid in a collection container or a wall of the container at a similar velocity, presenting a further opportunity to injure sperm.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a sperm sorting system that may include a sample source. At least one flow channel may be formed in a substrate and in fluid communication with the sample source. The at least one flow channel may include an inspection region, a first outlet, and a second outlet. At least one diverting mechanism may be in fluid communication with the at least one flow channel to selectively divert sperm away from the first outlet. An electromagnetic radiation source may be configured for illuminating sperm in the at least one flow channel at the inspection region and a detector may be aligned to measure sperm characteristics. An analyzer in communication with the detector may determine sperm characteristics and provide instructions to a controller for selectively activating the diverting mechanism. A collection vessel in communication with the second outlet may collect diverted sperm based on the measured sperm characteristics.

Another embodiment relates to a microfluidic chip for sorting sperm. The microfluidic chip can include a plurality of flow channels formed in a substrate. Each flow channel might include an inlet in communication with two outlets. Each flow channel may additionally include a fluid focusing region having an associated fluid focusing feature for aligning sperm cells within the flow channel, a sperm orienting region having an associated sperm orienting feature for orienting sperm cells within the flow channel, and an inspection region at least partially downstream of the fluid focusing region and the sperm orienting region. Additionally, a diverting mechanism may be in communication with each flow channel.

Another embodiment relates to a method of sorting sperm. The method may begin by flowing sperm through a plurality of flow channels in a microfluidic chip. Sperm may then be oriented within the microfluidic chip and flown through an inspection region. Sperm may be interrogated at the inspection region to determine sperm characteristics. Oriented sperm may be differentiated from unoriented sperm and/or non-viable sperm and a subpopulation of oriented sperm may be selected based on the detected sperm characteristics. The subpopulation of selected sperm may then be collected in the collection vessel.

BRIEF DESCRIPTION OF THE DRAWINGS

FIGS. 10A-D illustrate sectional views of a flow channel geometry in accordance with certain embodiments described herein.

FIGS. 11A-D illustrate sectional views of a flow channel geometry in accordance with certain embodiments described herein.

FIGS. 25A-D illustrate illumination and light collection features of flow channels in accordance with certain embodiments described herein.

Figure 1:
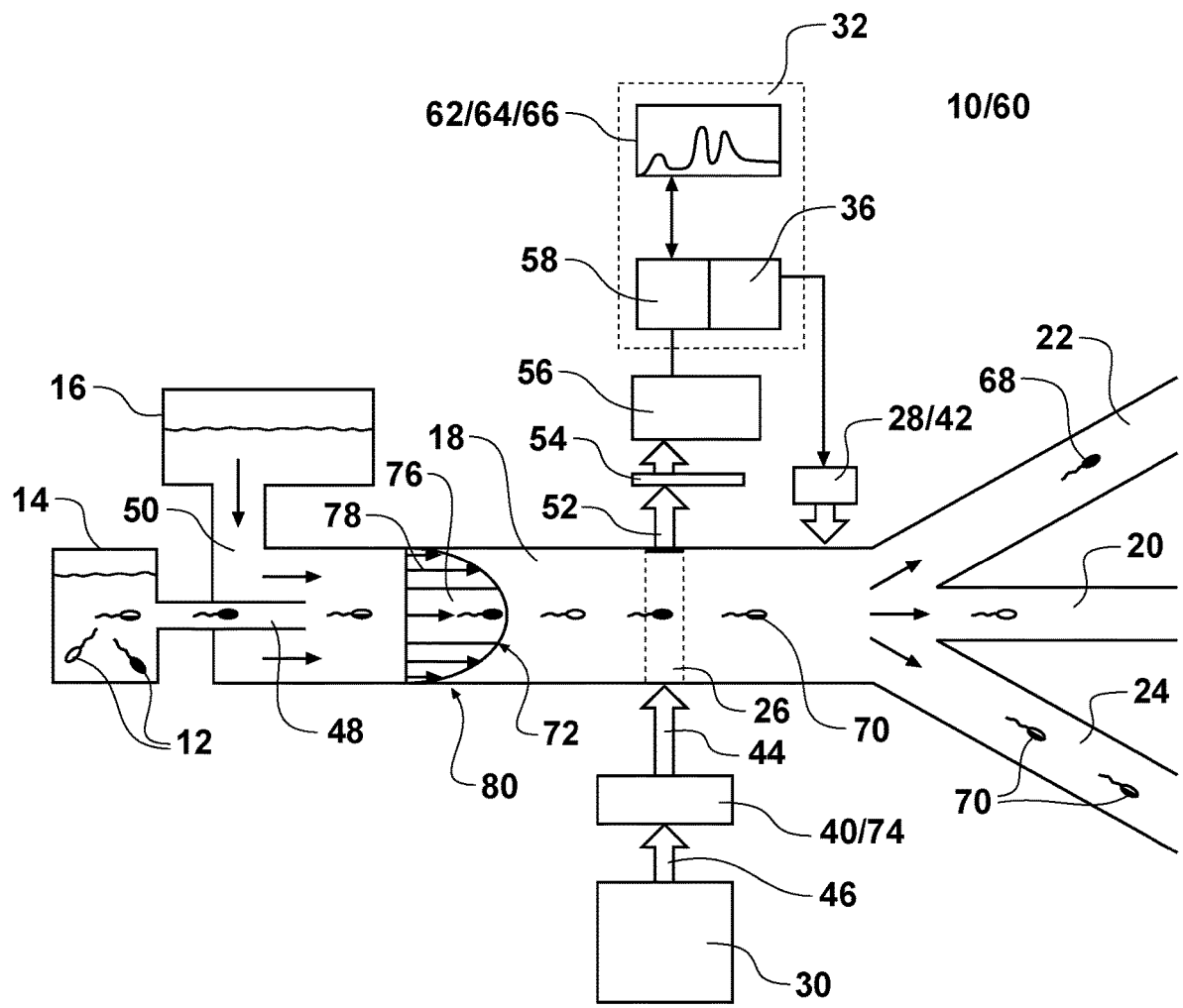
FIG. 1 illustrates a schematic of a single flow channel in sperm sorting micofluidic system in accordance with certain embodiments described herein.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

Certain embodiments described herein relate to a high throughput microfluidic system and device for sorting sperm, which overcomes deficiencies in the sorting speeds of prior devices with the inclusion of a plurality of parallel flow channels while maintaining the sperm in more gentle sorting conditions.

The term "flow channel," as used herein, refers to a pathway formed in or through a medium that allows the movement of fluids such as liquids or gasses. The flow channels of a micofluidic system may have cross sectional dimensions in the range of between about 1 micron and about 500 microns.

A "microfluidic system" may be considered a device that conveys particles of interest through one or more flow channels for the purpose of monitoring, detecting, analyzing, and/or sorting the particles of interest.

The term "viable" should be understood to refer to generally accepted projections of cell health. As one example, sperm sorting techniques employ a dual stain protocol in which a quenching dye differentially permeates membrane compromised sperm. Such a staining protocol distinguishes membrane comprised sperm from sperm which are generally healthier by permeating membrane compromised sperm cells and quenching the fluorescence associated with a DNA selective fluorescent dye. The permeation of the quenching dye is readily ascertainable in the course of analysis or sorting and may serve as a proxy for non-viable sperm. Although, some sperm which are quenched may be capable of fertilization, and some sperm which are not quenched may not be capable for fertilization, or may shortly thereafter loss the capability to fertilize. In either event, sperm which are unquenched in such a protocol provide one example of sperm which may be considered "viable" in conventional procedures.

As used herein the terms "beam segment" and "beamlet" should be understood to interchangeably refer to a portion of a beam of electromagnetic radiation spatially separated from another portion of the beam, where each portion may comprise a fraction of a beam profile, or may comprise beam portions split by conventional beam splitters, each having the same profile as the initial beam and a fraction of the intensity.

As used herein the terms "vertical," "lateral," "top," "bottom," "above", "below," "up," "down," and other similar phrases should be understood as descriptive terms providing general relationship between depicted features in the figures and not limiting on the claims, especially relating to flow channels and microfluidic chips described herein, which may be operated in any orientation.

Turning to the Figures, FIG. 1 illustrates a sperm sorting system including a high throughput sorting apparatus 10. The high throughput sorting apparatus 10 may be a fluidically enclosed device 60, such as a microfluidic chip 80, having at least one flow channel 18. Schematically, the flow channel 18 is illustrated as a single flow channel however; the flow channel 18 should be understood as at least one flow channel in the sorting apparatus. As a non-limiting example, between 4 and 512 flow channels may be formed in a single high throughput sorting apparatus 10. Each flow channel 18 may be formed in a chip substrate and may have interior dimensions of between 25 microns and 250 microns. The flow channels 18 may be spaced between about 100 and 3000 microns apart. The spacing of the flow channels 18 may depend on the ability of the system to detect fluorescence in each channel or on the space required to implement mechanical or electromechanical components to divert sperm 12 in the flow channel 18.

Sheath fluid may be supplied from a sheath source 16 and flowed into the flow channel 18 through a sheath inlet 50. Sperm 12 contained in a sample fluid may be supplied by, and initially located in, a sample source 14. Sample containing particles or cells of interest, such as sperm cells, may flow from the sample source 14 and into the at least one flow channel 18 through a sample inlet 48. The sample inlet 48 and the sheath inlet 50 may be configured such that a laminar, or nearly laminar, co-axial flow 72 develops in the flow channel 18. The coaxial flow 72 may consist of an inner stream 76, also referred to as a core stream, of sample and an outer stream of sheath fluid 78. Appropriate flow rates may be applied to both the sample source 14 and the sheath source 16 for establishing flow velocities, appropriate sample to sheath ratios, and particle event rates in the flow channel 18.

The velocity of particles in the coaxial flow 72 may be between about 1.5 m/s and about 5 m/s in the flow channel 18, as compared to between about 15 m/s and about 20 m/s in a droplet sorter. This lower velocity reduces the pressure to which the sperm cells are exposed, and perhaps more importantly reduces the sheering forces to which the particles are exposed in the flow channel 18. Additionally, the impact associated with collecting droplets is eliminated in the described system.

In one embodiment, the sample and sheath are established at pressures which provide a sample to sheath ratio of about 1:20. In certain embodiments, sheath fluid may be nearly eliminated or even entirely eliminated, resulting in little or no dilution. In contrast, droplet sorters tend to dilute sperm cells about 50:1 in sheath fluid and can even dilute sample as much as 100:1. These high dilution factors may contribute to dilution shock that may have a negative impact on the health of the sorted sperm.

Returning to FIG. 1, sperm 12 are illustrated passing through an inspection region 26 in the flow channel 18, where the sperm 12 are illuminated with an electromagnetic radiation source 30 and where emitted or reflected electromagnetic radiation 52 from the sperm 12 is captured by one or more sets of collection optics 54 having a suitable aspect ratio and numerical aperture for projection onto one or more detectors 56, which may interchangeably be referred to as sensors, for quantification by an analyzer 58. A sorting decision may be made in the analyzer 58 which is then passed through a controller 36 for actuating the appropriate response in a diverting mechanism 28. The diverting mechanism 28 may be a transducer 42, such as an ultrasonic transducer, for producing waves that divert cells in the flow path 18. The transducer 42 may also be a piezoelectric element forming a portion of an actuator. The diverting mechanism 28 may direct sperm into any or a first outlet 20, second outlet 22, and a third outlet 24. Although, in one embodiment the diverting mechanism 28 may direct sperm into only a first outlet 20 or a second outlet 22.

Electromagnetic radiation 46 emitted by the electromagnetic radiation source 30 may be manipulated by beam shaping optics 40 and/or a beam splitting device 74 in free space to produce one or more manipulated beam(s) 44, which may also be referred to as beamlets or beam segments 44. A suitable electromagnetic radiation source may include a quasi-continuous wave laser such as a Vanguard 355-350 or a Vanguard 355-2500 model laser available from Newport Spectra Physics (Irvine, Calif.). A manipulated beam in the form of one or more beamlets may be purposefully altered to provide uniform intensity, power, and/or geometry from one beamlet to the next beamlet. Each beamlet intensity profile may additionally be highly uniform in one or more axes. For example each beamlet may have a "top-hat" or "flat top" beam profile, although other profiles may also be used. In one embodiment, each beamlet profile may also have a Guassian distribution in one or more axes. Each beamlet may have an elliptical, circular, rectangular or other suitable shape. Each beamlet may also have an aspect ratio, axis of symmetry or other suitable profile. Alternatively, beamlet intensity profiles may be varied in a non-uniform manner. In one embodiment, a plurality of fiber optics may be employed to deliver multiple beams to one or more flow channels.

The electromagnetic radiation source 30 may be a common source of electromagnetic radiation divided among each of several flow channels 18. As one example, the beam splitting device 74 may be a segmented mirror, such as the one described in U.S. Pat. No. 7,492,522, the entire contents of which are incorporated herein by reference. The segmented mirror may divide the electromagnetic radiation 46 into a plurality of beamlets, each beamlet being directed to a respective inspection region 26 of the at least one flow channel 18. In additional embodiments, a partial transmission element may be incorporated into light paths in free space or as part of a fiber cable. The partial transmission element may include pass-through apertures and/or blocking regions to obtain an ultimate beam profile suited to excite sperm cells in the inspection region. Partial transmission elements may be positioned within an optical train, or alternatively they may be incorporated onto or within a chip substrate. Such an element may include more than one transmission region per flow channel. As a non-limiting example, pairs of rectangular apertures along a flow axis may sequentially illuminate sperm cells in a flow path.

The analyzer 58 and controller 36 may be two separate components, or may represent two functions performed by a single component, such as a processing device 32. For example, one or more memories connected through a bus to one or more processors may execute written computer instructions to perform each of the functions described with respect to the controller 36 and the analyzer 58. Non-limiting examples of suitable processing devices 32 include personal computers and other computing systems. The analyzer 58 may be in communication with a user interface 62, which may include a display 64 and an input 66. The user interface 62 may graphically display various sorting parameters and provide a visual feedback for adjusting one or more of sort parameters. As a non-limiting example, a sort logic may comprise the logic applied to each sort decision. The sort logic may be adjusted by a user at the user interface 62 based on sorting data generated on the display 64 or based on a visual representation of sort data provided at the user interface 62. The types of adjustments which may be made to the sort logic may include adjusting gating regions, adjusting the strategy for dealing with coincident events, and/or adjusting the sort envelopes associated with each potential sort decision.

As an illustrative example, sperm may be identified as viable X-chromosome bearing sperm, viable Y-chromosome bearing sperm, or as particles which are not desirable for collection, such as waste and unoriented sperm. In one embodiment, the coaxial stream flows to the first outlet 20 by default and the first outlet 20 is in communication with a vessel for collecting waste. In this configuration, the vessel in communication with the first outlet 20 may also be a passive collection vessel, in that sperm are collected in this vessel when no action is taken. Particles which are positively identified as either viable X-chromosome bearing sperm 68 or viable Y-chromosome bearing sperm 70 may be actively diverted by a diverting mechanism 28. Actuation of the diverting mechanism may be timed using calculated velocities, as well as individually measured velocities and aggregated velocities for a number of sperm. Viable X-chromosome bearing sperm 68 may be diverted into the second outlet 22, whereas viable Y-chromosome bearing sperm 70 may be diverted into the third outlet 24.

Figure 2A:
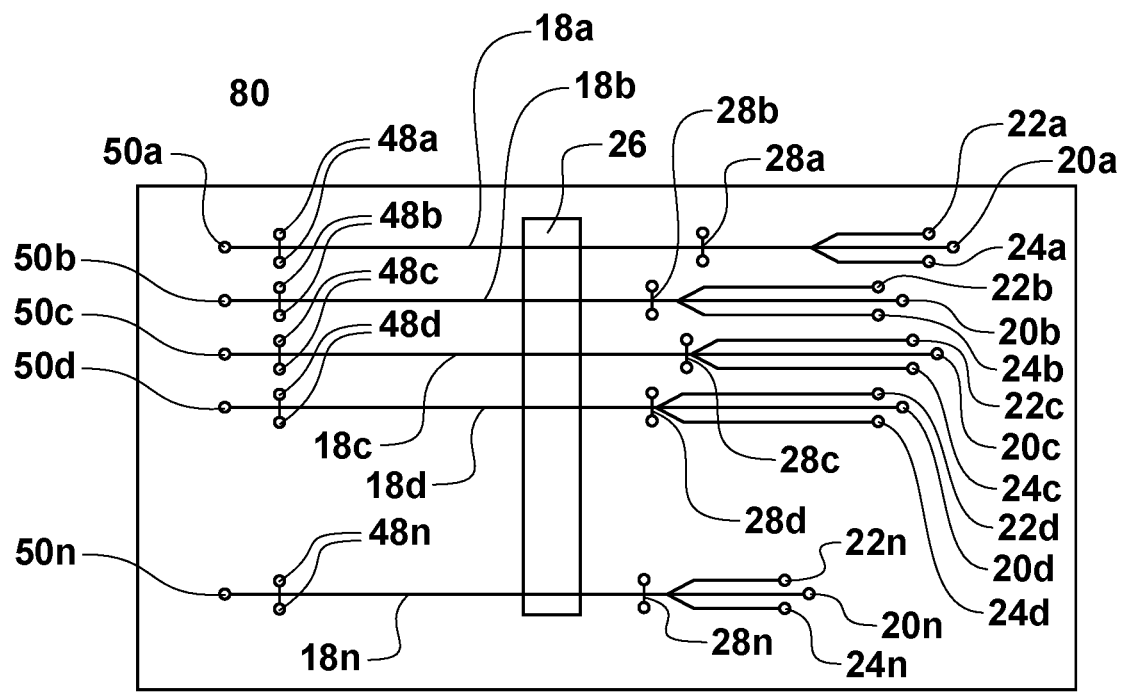
FIGS. 2A-C illustrate an arrangement of flow channels on a microfluidic chip in accordance with certain embodiments described herein.

Turning to FIG. 2A a portion of a sperm sorting system 10 is illustrated in the form of a microfludic chip 80 having several flow paths 18a, 18b, 18c, 18d, and 18n, which are each generally in parallel. Each flow channel 18 may be fluidically connected to the sample and sheath as well as to collection vessel forming a fluidically enclosed device 60. Each flow channel 18 has a sample inlet 48 and a sheath inlet 50 as described with respect to FIG. 1 for establishing coaxial flow therein. An inspection zone 26 is provided across each of the flow channel 18. A specific diverting mechanism is illustrated in the form of a bubble valve for diverting particles flowing in the flow channel 18. The bubble valves may be like those described in U.S. Pat. No. 7,569,788, the entire contents of which are incorporated herein by reference. The bubble valves may be operated in each flow channel 18 for allowing particles to flow through the first outlet 20 of each channel 18, or for diverting particles into the second outlet 22 or the third outlet 24 of each channel 18. It should be appreciated, bubble valves are provided in this figure for illustrative purposes and that other diverting mechanisms 28, such as mechanisms for deflecting cells with acoustic waves and mechanisms to facilitate deflecting particles with electromagnetic radiation may also be incorporated.

Figure 2B:
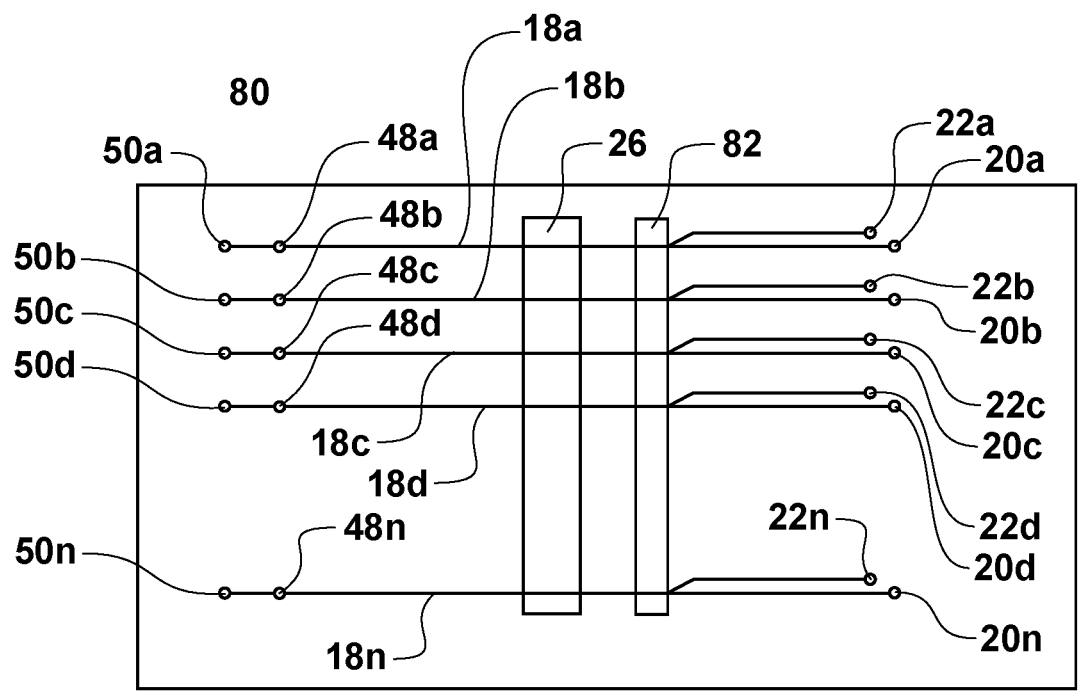

FIG. 2B illustrates different features, which may be interchangeable and need not be used together. Each of the flow channels 18 is illustrated with only first 20 and second outlets 22. Such a configuration may be used for collecting for cells with a single desired trait, such collecting only viable X-chromosome bearing sperm or viable Y-chromosome bearing sperm. An array of ultrasonic transducers 82 is illustrated downstream of the inspection region 26 and for the purpose of selectively diverting sperm cells. The array of ultrasonic transducer 82 may be embedded within the microfluidic chip 80 or they may be placed on the exterior of the microfluidic chip 80. Regardless of positioning, the array of ultrasonic transducers 82 may comprise a series of independent ultrasonic transducers 42 which are independently activated by the controller 36 for diverting sperm cells on demand to their respective outlets in parallel flow channels 18. Multiple ultrasonic transducers may be arranged in arrays or other formations along the direction of flow for a given flow channel to enable multiple actuations to be applied to a given particle as it travels along the flow channel towards a selection region, or branch leading to multiple outlets. Fluid outlets may interface with a suitable coupling ship holder element and provide suitable manifold features to maintain fluidic isolation or to pool various outlet fluids.

Figure 2C:
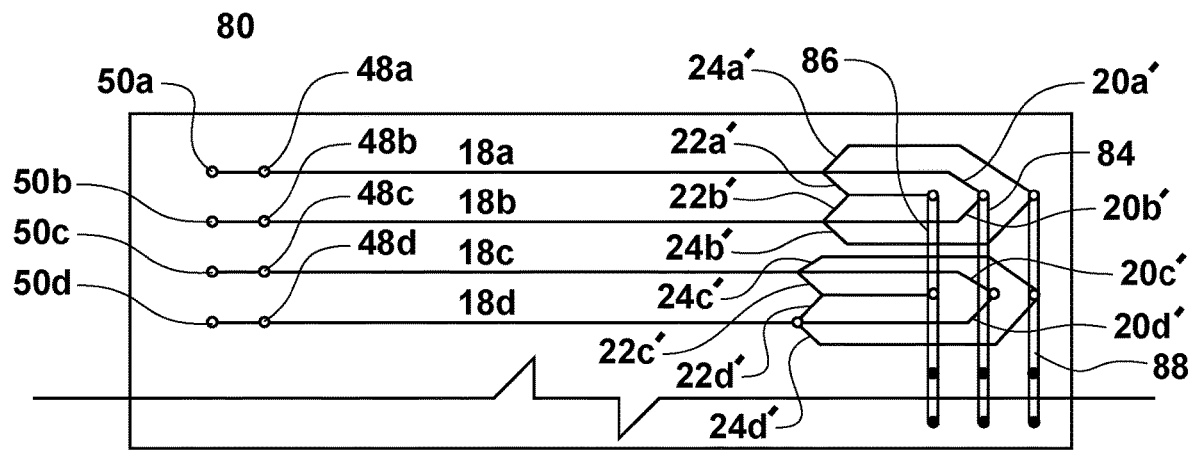

FIG. 2C illustrates alternative configurations of the channels and the outlets. Pooling channels may be fabricated with the microfluidic chip 80 for the collection and pooling of common outputs. In one embodiment, adjacent outlets are merged in flow the first flow channel 18a, second flow channel 18b, third flow channel 18c, and fourth flow channel 18d. The sorting logic may be adjusted according to different chip configurations to ensure the second and third outlets, respectively, collect the same particles in each fluid stream. For example, the first outlet 20a' of the first flow channel 18a merges with the first outlet 20b' of the second flow channel 18b. Downstream of each merging point, the single channel which receives fluid from both outlets may be pooled in a first pooling channel 84. The first pooling channel 84 may be formed a different layer of the microfluidic chip 80 to allow pooling from multiple merged outlets. The first pooling channel 84 may be in fluid communication with a first common collection vessel. The first pooling channel 84 is additionally illustrated in a configuration for collecting fluid from the first outlet 20c' of the third flow channel 18c, the first outlet 20d' of the fourth flow channel 18d.

Similarly, a second pooling channel 86 is illustrated in communication with the merged second outlet 22a' of the first flow channel 18a and second outlet 22b' of the second flow channel 18b as well as with the merged second outlet 22c' of the third flow channel 18c and second outlet 22d' of the forth flow channel 18d. The second pooling channel 86 may be in fluid communication with a second common collection vessel. A third pooling channel 88 is illustrated in communication with the merged third outlet 24a' of the first flow channel 18a and third outlet 24b' of the second flow channel 18b as well as with the merged third outlet 24c' of the third flow channel 18c and third outlet 24d' of the forth flow channel 18d. The third pooling channel 88 may be in fluid communication with a third common collection vessel.

Turning now to FIGS. 3A-3D one embodiment of the diverting mechanism 28 is depicted in action. Sample containing sperm cells 12 may be supplied through a sample inlet 48 and injected into a sheath fluid flow provided by the sheath source 16 through the sheath inlet 50. The flow channel 18 carries sperm 12 through the inspection region 26, where the cells are illuminated by the electromagnetic radiation source 30 and where sperm characteristics are determined by the analyzer 58 in communication with the detector 56.

Two opposed diverting mechanisms 28 are illustrated in the form of a first bubble valve 90a and a second bubble valve 90b downstream of the inspection region 26. The bubble valves 90 are spaced opposite each other, although those of ordinary skill will realize that other configurations can also be used. The first and second bubble valves 90a and 90b are in fluid communication with the flow duct 18 through a first side passage 94a and a second side passage 94b, respectively.

Liquid, generally sheath fluid, fills these side passages 94a and 94b providing fluid communication between the flow channel 18 and a membrane 96 associated with each. The membrane 96 may be in the form of a meniscus or other flexible material, including elastic materials. The membrane 96 defines an interface between the sheath fluid and another volume of fluid 98, such as a gas or gel in a fluid chamber 100 of the associated bubble valve 90. An actuator may be provided for engaging either bubble valve 90, which momentarily causes a flow disturbance in the flow channel 18 and deflects flow therein when activated. As illustrated, an actuator is coupled to the first bubble valve 90a and the second bubble valve 90b. One bubble valve 90 may serve as a buffer for absorbing the pressure pulse created by the other bubble valves 90 when activated. Alternatively, an actuator may be in communication with only one bubble valve 90 for deflecting particles or cells in a single direction. Alternatively, an actuator may be in communication with a single bubble valve for deflecting particles in more than one direction. As will be described in more detail later, a single bubble valve may be configured to selectively push or pull the trajectory of particles along their fluid path. The actuators may be pins configured for actuating any one of the groups of bubble valves in multiple flow channels 18. Pins may be configured in a number of arrangements to accommodate different configurations, like those depicted in FIGS. 2A-2C. An illustrative example of an actuator for actuating pins individually for deflecting particles in multiple parallel channels is described in U.S. Pat. No. 8,123,044, the entire contents of which are incorporated herein by reference.

The first side passage 94a is hydraulically connected to a fluid chamber 100a in the first bubble valve 90a, so that as pressure exerted in this chamber is increased, the flow in the flow channel 18 near the side passage 94a is displaced away from the side passage 94a, substantially perpendicular to the normal flow in the flow channel. The second side passage 94b, positioned opposite of the first side passage 94a, is hydraulically connected to a second fluid chamber 90b in the second bubble valve 90b and may absorb pressure associated with the perpendicular displacement caused by the first bubble valve 90a. This first side passage 94a cooperates with the second side passage 94b to direct the before mentioned liquid displacement caused by pressurizing the fluid chamber 90a, so that the displacement has a component perpendicular to the normal flow of the particles through the flow channel 18. In an alternative embodiment, a single bubble valve may be used without a cooperating second bubble valve.

The cooperation of the two side passages 94 and fluid chambers 100 causes the flow through the flow channel 18 to be transiently moved sideways back and forth upon pressurizing and depressurizing of the either fluid chamber 100 by the external actuator. Based on the detected sperm characteristics, an actuator on either bubble valve 90 may be driven by the controller 36 and can be applied in deflecting sperm having predetermined characteristics to separate them from the remaining particles in the sample.

The flow channel 18 is illustrated with a first branch leading to a first outlet 20 that is generally parallel with the existing flow channel 18. The first outlet 20 may be a default outlet to which particles will flow unless one of the bubble valves 90 is activated. A second outlet 22 may branch away from the first outlet 20 some distance downstream of the inspection region 26. Similarly, a third outlet 24 may be reached through a branch generally on the opposite side of the flow channel 18 as the first branch. The angle between the branches extending to the second 22 and third outlets 24 may be separated between 0 and 180 degrees, or even between 10 and 45 degrees.

The sperm cells 12 supplied from the sample source 14, may contain multiple types of cells which may be differentiated by the analyzer 58. In the case of sperm 12, there may be viable X-chromosome bearing sperm 68, viable Y-chromosome bearing sperm 70, and undesirable particles. The undesirable particle may include dead sperm, unoriented sperm which could not be identified, other particles, or sperm cells which are not sufficiently spaced in the flow channel for separation.

Upon sensing a predetermined characteristic in a sperm cell 12, illustrated as an X-chromosome bearing sperm 68, the analyzer 58 may provide a signal to the controller 36 for activating the appropriate external actuator at an appropriate time, which in turn engages the second bubble valve 90b to cause pressure variations in the fluid chamber 100b. This pressure variation deflects the membrane 96b in the second bubble valve 90b. The first side passage 94a and the first bubble valve 90a absorb the resulting transient pressure variations in the flow channel 18 resulting in a diverting force in the flow chamber 18, which is timed to divert the X-chromosome bearing sperm cell 68 to a different position in the flow channel 18 (seen in FIG. 3B). The fluid chamber 90a of the first bubble valve 90a may have a resilient wall, such as a meniscus, or may contain a compressible fluid, such as a gas or gel. The resilient properties allow the flow of liquid from the flow channel 18 into the first side passage 94a, allowing the pressure pulse to be absorbed providing a narrow window in which cells are diverted and preventing disturbance to the flow of the non-selected particles in the stream of particles. Similarly, in the event a Y-chromosome bearing sperm 70 is detected an external actuator may be utilized to pressurize the first bubble valve 90a and divert the sperm cell to the third outlet 24. Alternatively, either Y-chromosome bearing sperm, X-chromosome bearing sperm, or even both may be passively sorted by being allowed to pass through to the first outlet while undesirable sperm is deflected away from the first outlet.

Figure 3A:
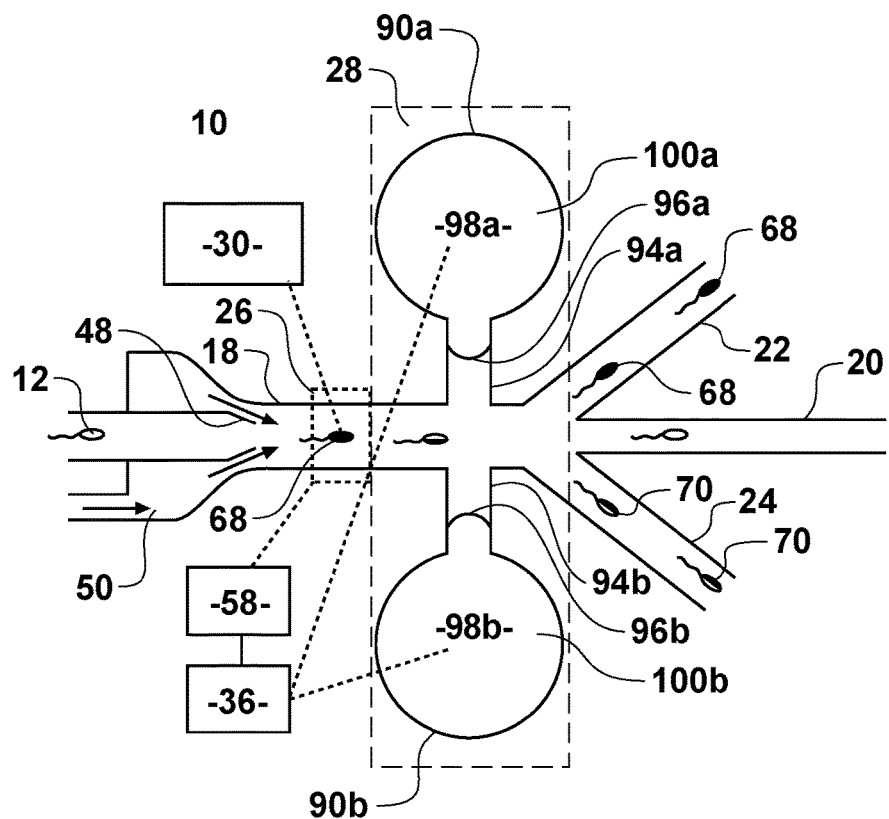
FIGS. 3A-D illustrate the operation of a diverting mechanism in accordance with certain embodiments described herein.
Figure 3B:
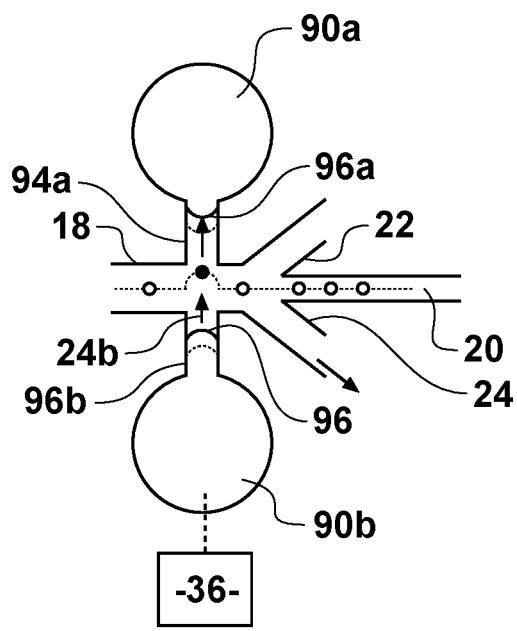
Figure 3C:
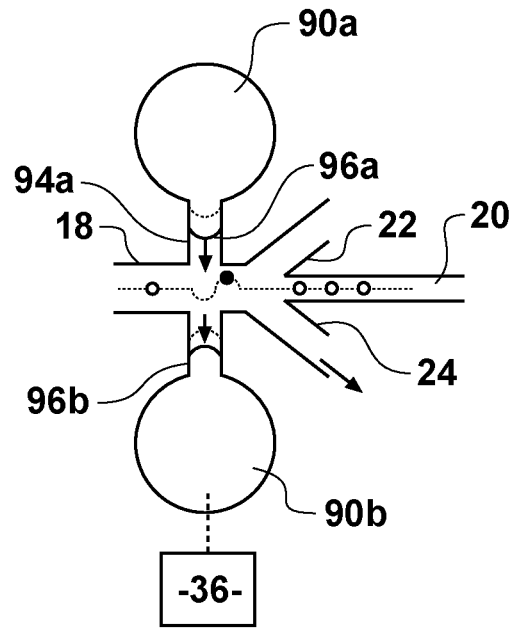

FIG. 3C illustrates a period immediately following deflection the second bubble valve 90b when the particle of interest, shown as the same viable X-chromosome bearing sperm 68, has left the volume between the first side passage 94a and the second side passage 94b. Following such an activation the pressure inside the both fluid chambers 100 returns to normal and each membrane 96 returns to an equilibrium position while sheath fluid exits the first side passage 94a and reenters the second side passage 94b as indicated by the arrows.

Figure 3D:
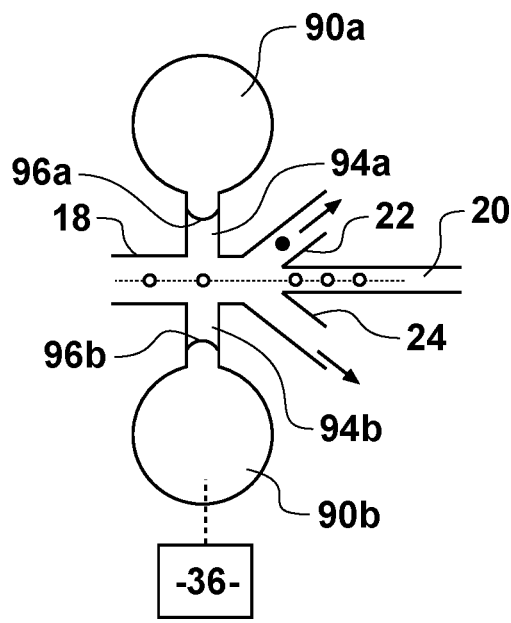

FIG. 3D illustrates the system 10 after completion of the switching sequence. The pressures inside the fluid chambers 100 of each bubble valve 90 are equalized, allowing the flow through the flow channel 18 to normalize so that undeflected sperm continue toward the first outlet 20. Meanwhile, the particle of interest, still illustrated as a viable X-chromosome bearing sperm cell, has been displaced from its original trajectory, and flows into the first branch and the second outlet 22, while the other cells may continue undeflected towards the first outlet 20, thereby separating the particles based on the predetermined characteristic.

In an alternative embodiment, one or both of the first bubble valve 90a and the second bubble valve 90b may be preloaded with pressure by an actuator. In response to sort decisions generated by the analyzer 58 and sort actions from the controller 36, the actuator may be unloaded from either bubble valve 90 in order to retract the respective membrane 96, draw additional sheath fluid into the respective side passage 94 in order to deflect the trajectory of a sperm cells towards that side passage 94.

Figure 4A:
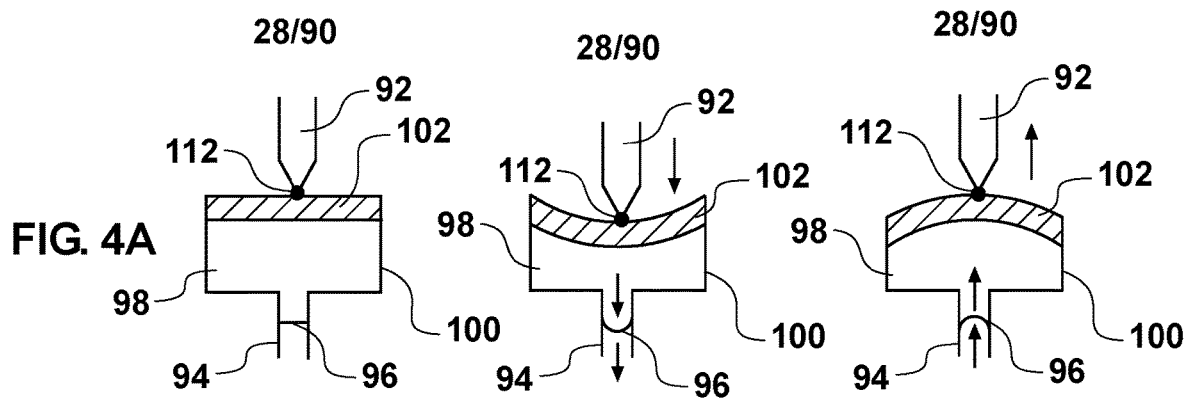
FIGS. 4A-C illustrate alternative diverting mechanisms in accordance with certain embodiments described herein.

Referring now to FIG. 4A, one embodiment of a diverting mechanism 28, and in particular one embodiment of the bubble valve 90, is depicted in which an actuator 92 is affixed to a flexible interface 102 at an attachment point 112. The flexible interface 102 may be fluidically sealed with the fluid chamber 100, or may actuate an intermediate component which in turns causes actions like those described below. In a first position, which may be considered a resting position, the actuator 92 and the flexible interface 102 are at rest, so that the fluid 98 in the fluid chamber 100 does not deflect the membrane 96 into the side passage 94. In a second position, which may be considered a first activation position, the actuator 92 may be driven into the flexible interface 102, causing the flexible interface 102 to intrude into the volume of the fluid chamber 100 such that pressure is applied on the membrane 96 and fluid is expelled from the side passage 94. This expelled sheath fluid provides the pressure pulse which may deflect particles, like sperm, away from the side passage 94.

When the actuator 92 is attached to the flexible interface 102 at an attachment point 112, a third position, which may be considered a second activation position, is possible whereby the actuator 92 pulls the flexible interface 102 away from the fluid chamber 100 expanding the volume (in the case of compressible fluids) such that the membrane 96 is drawn in and additional sheath fluid is drawn into the side passage 94. The resulting pressure pulse may draw sperm or other particles towards the side passage 94 in the flow channel 18. It should be appreciated that the volumes of the fluid chambers 100, the type of fluid 98, and the dimensions of the side passage 94 may be modified to achieve desired deflections in the flow channel 18. It should further be appreciated, the second position and the third position, may be considered the extreme positions, and that a multitude of intermediate positions are also contemplated between the two extreme positions. For example, the flow channel 18 may comprise four, five, six or more branches, each of which may be capable of receiving particles properly deflected by the bubble valve 90.

Figure 4B:
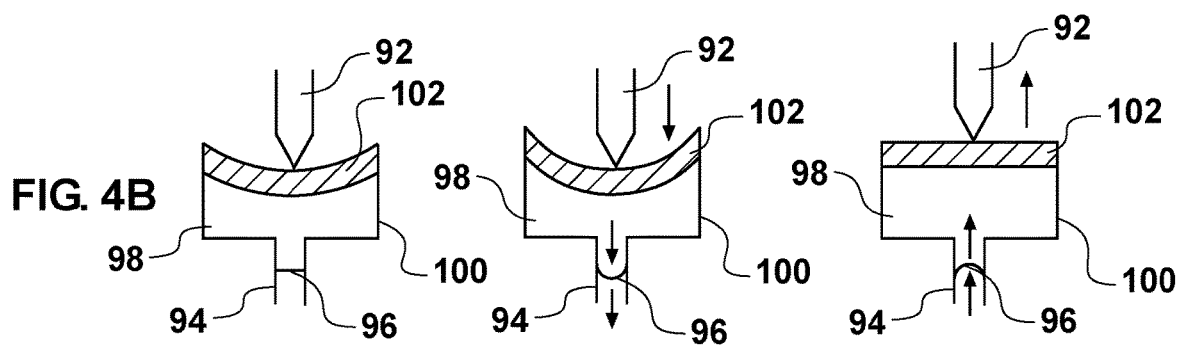

FIG. 4B provides an alternative embodiment, whereby the actuator 92 is preloaded onto the flexible interface 102. Stated differently, the fluid chamber 100, the fluid 98, and the membrane 96 may be considered to be in a resting position while there is some deflection of the flexible interface 102 into the fluid chamber 100 volume. The actuator 92 may be further driven into the flexible interface 102 to a first activation position, which acts on the fluid 98 to displace the membrane 96 and expel sheath fluid from the side passage 94.

Moving the actuator 92 outwards, to the second activation position, may act to draw the membrane 96 inwards and draw fluid into the side passage 94. In such an embodiment, moving the actuator 92 into a position, which may appear to be a resting position, may accomplish a pressure pulse for deflecting particles. In the depicted embodiment, this displacement may result in a pressure pulse which draws particles towards the side passage 94. However, an attachment point 112 may be provided between the actuator 92 and the flexible interface 102, and the flexible interface 102 such that the flexible interface 102 can be preloaded in the opposite direction.

Figure 4C:
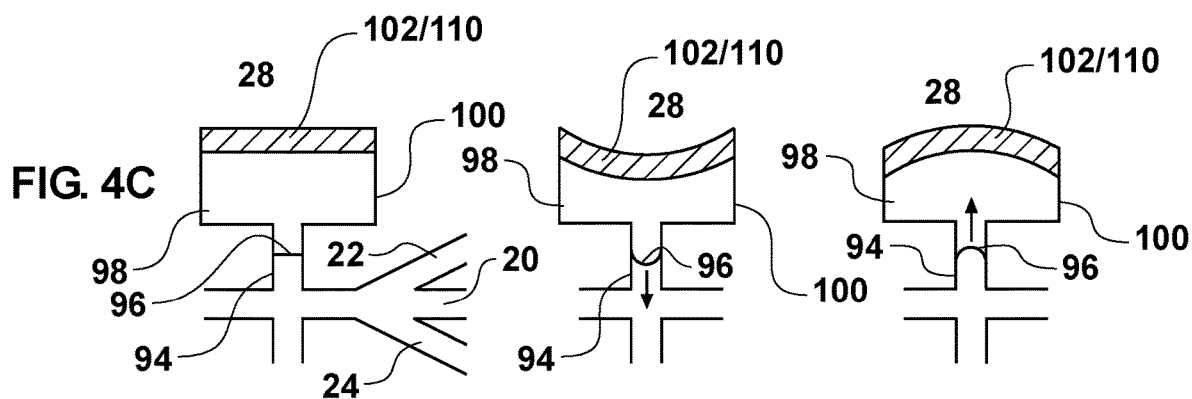

FIG. 4C depicts one alternative embodiment of a bubble valve in which the flexible interface 102 may comprise a bimorph piezoelectric element 110. The bimorph piezoelectric element 110 may be provided in a sealed relationship with the fluid chamber 100, or may rest against another flexible material which is sealed against the fluid chamber 100 and through which motion of the bimorph piezoelectric element 110 is translated. In a resting position, the bimorph piezoelectric element 110 may be at rest, such that particles pass the side passage 94 undeflected. In response to a control signal the bimorph piezoelectric element 110 may bend into a first activation position intruding into the fluid chamber volume 100 and causing the membrane 96 to expel out of the side passage 94. The resulting pressure pulse may deflect particles away from the side passage 94 and the bubble valve 90. Similarly, the bimorph piezoelectric 110 may be provided with a signal causing the element to deflect or bend into a second activation position. The second activation position may act upon the fluid 98, fluid chamber 100, and membrane 96 in a manner that draws fluid into the side passage 94. In this way, particles may be deflected towards the side passage 94.

The bimorph piezoelectric element 110 may be precisely controlled by electrical signals in degree of deflection and timing. For example, any number of intermediate positions between the first and second activation positions may be achieved for deflecting particles with a variety of trajectories. The bimorph piezoelectric element 110 may only require an electrical connection, thereby potentially simplifying spacing issues which may otherwise exist.

Figure 5:
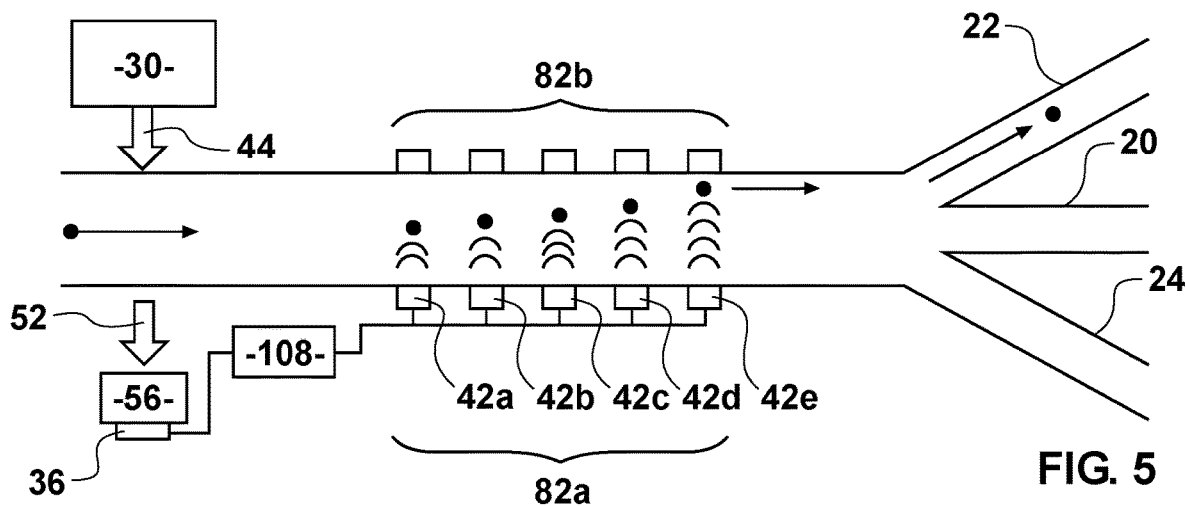
FIG. 5 illustrates an alternative diverting mechanism in accordance with certain embodiments described herein.

While bubble valves present a viable diverting mechanism, other diverting mechanisms 28 are contemplated for use with certain aspects of the microfluidic chip described herein. An alternative arrangement is illustrated in FIG. 5, which shows a particle being diverted by the activation of transducers 42, such as piezoelectric elements or ultrasonic transducers. Each transducer 42 may form a portion of an array of transducers 82. Each transducer 42 in the array of transducers 82 may be sequentially activated based on expected or calculated particle velocity to provide pulses which act on the particle at multiple points along the flow channel 18.

An electromagnetic radiation source 30 may provide electromagnetic radiation for inspecting particles. A fluorescence, scatter, or other responsive emission may be detected by one or more detectors 56, and processed by analyzer 58. Resulting sort decisions may be conveyed from a controller 36 through a driving element 108 to each transducer 42. The driving element 108 may provide the timed activation of transducers 42 for interacting with a sperm cell or other particle multiple times along the flow channel 18. Each transducer 42 may be an acoustic transducer, or even an ultrasonic transducer, and the frequency at which the transducers are drive may be optimized for producing a deflection of particles, or even more specifically for deflecting or diverting sperm in the flow channel 18. In one embodiment, each transducer 42 may provide a single pulse directed to divert the particle, while in another embodiment, each transducer may produce multiple pulses directed to divert the particle. In still another embodiment, one or more arrays of transducers 82 may be operated to produce a standing wave in the flow channel 18. As a diverting mechanism 28 the standing wave may attract or repel particles within certain nodes or antinodes of the acoustic field. In one embodiment, the transducers 42 are operated in the range of 10-16 MHz.

In one embodiment, an array of transducers 82 is present on each side of the flow channel 18 for diverting particles in both directions. In another embodiment, a single array of transducers 82 may be incorporated for the purpose of deflecting particles or sperm cells in both directions. The array of transducers 82 may be embedded within a chip substrate, or they may be located on an external surface of a microfluidic chip 80. Additional, the array of transducers 82 may be removable from the chip 80.

In an alternative embodiment, an array of optical elements may be incorporated in a similar manner to divert particles with a radiation pressure. A single laser, or other source of electromagnetic radiation may be gated or staged in a manner that allows multiple applications to a single particle traveling along the flow channel, or which rapidly follows particles in the flow channel 18. Alternatively, multiple lasers may be used to deflect a particle with several applications of radiation pressure.

Figure 6:
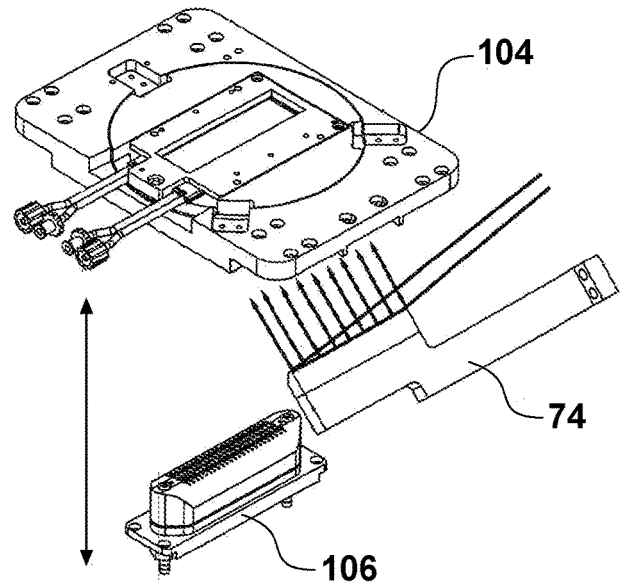
FIG. 6 illustrates a chip holder and beam separator in accordance with certain embodiments described herein.

Turning now to FIG. 6, a chip holder 104 is illustrated for holding a microfluidic chip 80 in a precise position so that an actuator block 106 and shaped/separated beam may precisely engage the diverting mechanisms 28 and inspections regions 26, respectively. A beam splitting deice 74 is illustrated for producing multiple beam segments, each of which may be aligned with a flow channel 18 generally perpendicular to the flow channel 18 or at an angle. The chip holder 104 may include a mechanism for firmly securing the microfluidic chip 80 in a relative position, or may include mechanisms for adjusting the relative position of the microfluidic chip 80, such as for aligning the flow channel in the chip with detectors and illumination sources.

Figure 7:
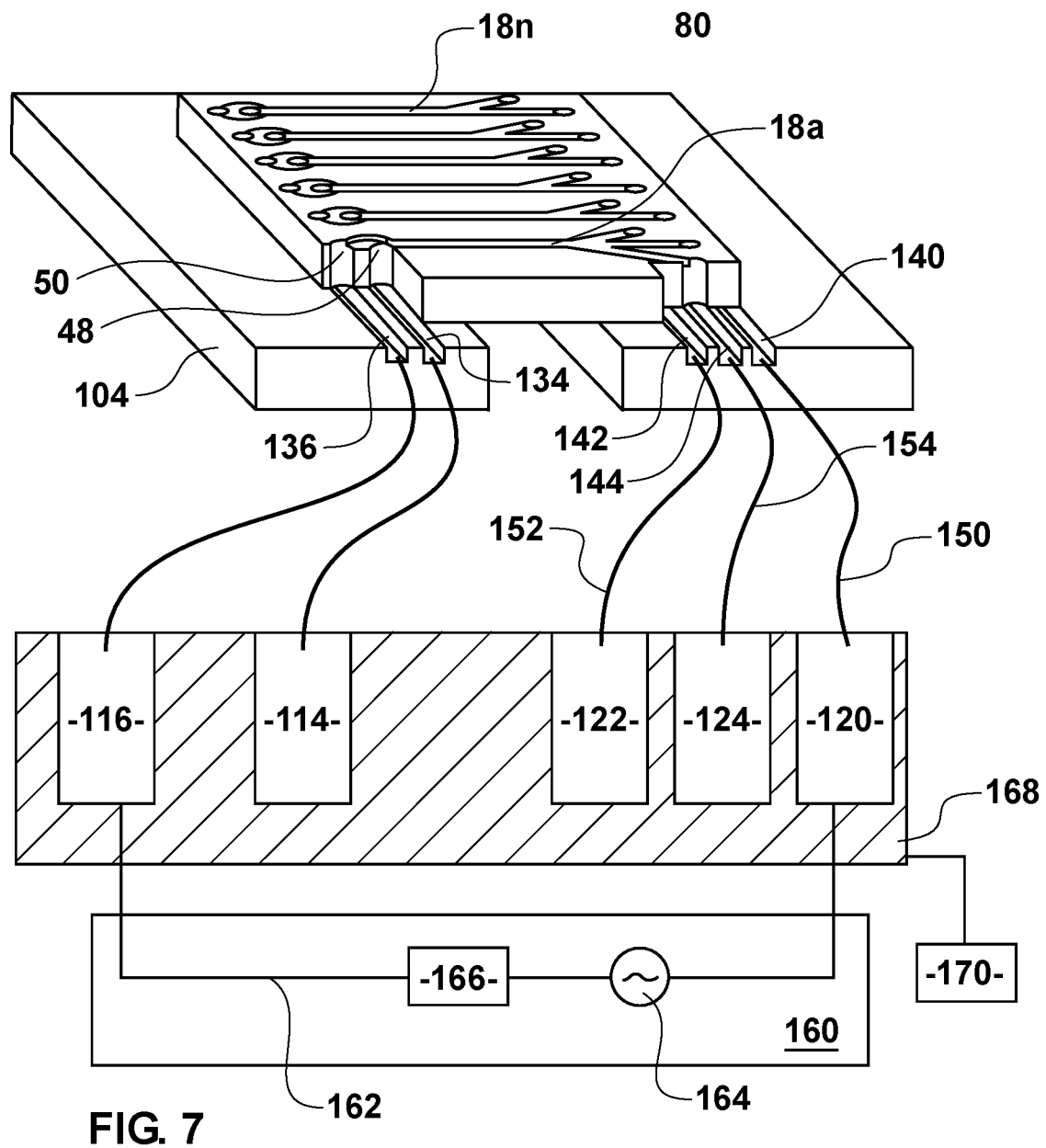
FIG. 7 schematically illustrates a chip, chip holder and cartridge in accordance with certain embodiments described herein.

Turning now to FIG. 7 an embodiment of a microfluidic chip 80 is illustrated on a chip holder 104 in conjunction with a fluidics system in the form of a cartridge 168. It should be appreciated, some features illustrated formed in portions of the chip holder 104 may also be integrated into an additional layer of the microfluidic chip 80 itself. The microfluidic chip 80 is illustrated with multiple flow channels 18 having a sheath inlet 50 and a sample inlet 48, in addition to a first outlet 20 a second outlet 22 and a third outlet 24 in each channel.

The cartridge 168 may comprise a series of reservoirs in fluid communication with the microfluidic chip 80 and/or the chip holder 104. The cartridge 168 may be formed from a polymer or other suitable biocompatible material and each reservoir is contemplated to directly hold fluids, or to hold bladders or other sealable containers filled with fluids. A sample reservoir 114 may be a fluidically sealed reservoir in fluid communication with a sample channel 134 in the chip holder 104. The fluidic connection between the sample reservoir and the sample channel 134 may be performed in sterile conditions to prevent or reduce exposure of the sample to pathogens and bacteria. Similarly, a sheath reservoir 116 may be fluidically connected to a sheath channel 136 in the chip holder 104. Each of the reservoir may have an associated transport mechanism. As one example, fluid may be transported via pressure gradients created at each reservoir. The pressure gradients may be created with pumps, peristaltic pumps, and other similar means.

A cut away portion of FIG. 7 illustrates the connection of the sheath channel 136 and the sample channel 134 to their respective inlets and to the first flow channel 18b. While not illustrated, the remaining flow channels 18b through 18n may have similar fluidic connections to reservoirs through the channels. In this manner, each flow channel 18b through 18n may be supplied from a common sample reservoir 114a nd from a common sheath reservoir 116 to facilitate the parallel operation of multiple channels in a microfluidic chip 80.

The cartridge 168 may contain additional reservoirs for processed fluids. As an example, the cartridge 168 may contain a passive collection reservoir 120, a first active collection reservoir 122 and a second active collection reservoir 124. The passive collection reservoir 120 may be in fluid communication with the first outlet 20 of each channel 18 through a passive collection channel 140 where fluid pools from each first outlet 20 and is fed through a passive collection line 150. In one embodiment, the passive collection may be the default collection and may include waste and/or undesirable particles. Similarly, the first active collection reservoir 122 may be fluidically connected to the second outlet 22 of each flow channel 18 through a first active collection channel 142 and a first active collection line 152 and a second active collection reservoir 124 may be connected to the third outlet 24 though a second active collection channel 144 and a second active collection line 154. A second cut away illustrates the relationship between the third outlet 24 and the second active collection channel 144, which will be similar for each flow channel 18. Fluids and sperm cells, whether actively or passively sorted, may be drawn through each respective outlet, channel, line and reservoir by a transport mechanism, such as a pressure gradient.

As an illustrative example, the channels in the microfluidic chip 80 may have widths between about 20 µm and about 400 µm, while the channels in the chip holder may have widths between about 200 µm and about 2 mm. The lines connecting each channel to their respective reservoirs may have inner diameters between about 0.25 mm and about 5 mm.

One embodiment provides an optional sheath fluid recycling system 160 for recycling sheath fluid from the waste reservoir. FIG. 7 illustrates a recycling line 162 providing fluid communication from the passive collection reservoir 120 to the sheath reservoir 116. A pump 164 may be provided in the recycling line to drive fluid through a concentrating system 166, such as a filter, and on to the sheath reservoir 116. Alternatively, the passive collection reservoir 120 and the sheath reservoir 116 may be provided at differing pressures that tend to drive fluid from the passive collection reservoir 120 through the recycling line 162 and to the sheath reservoir 116. Alternatively other transport mechanisms may be incorporated to convey fluid from one of the collection reservoirs to the sheath reservoir 116. In one embodiment, the filter may be replaced by other cell concentrating systems 166, or by systems for removing fluid or supernatant. In one embodiment, a series of filters may be used for conditioning sheath fluid as appropriate for a specific application, such as sperm sorting. Further non-limiting examples of sperm concentrating systems may include centrifugation systems, microfluidic unites, porous membranes, spiral concentrators, or hydrocyclones, or other particle concentrating devices or fluid removing systems. In still another embodiment, the cell concentrating system 166 may provide actively collected sperm in one or both of the first 122 and second 124 active collection reservoirs at an appropriate concentration for further processing, while providing supernatant sheath fluid back to the sheath reservoir 116. As one example sperm may be concentrated to an appropriate dosage for receiving a freezing extender, or sperm may be concentrated to an appropriate dosage for performing AI, IVF or another assisted reproductive procedures.

Yet another feature that may be present in some embodiments is a temperature regulating element 170. The cartridge 168 may perform heating and/or cooling of any or all fluids stored thereon. For example, the temperature regulating element 170 may take the form of heating and/or cooling pads or regions on the cartridge 168. Each chamber or reservoir of the cartridge 168 may be held at different temperatures or have its temperature modified during operation. Any suitable means for controlling the temperature within a selected chamber or region of the unitary particle processing cartridge may be used. In a sperm sorting embodiment it may be desirable to maintain sperm at a relatively constant temperature, such as a cool temperature, as much as possible. It may further be desirable to cool sperm for the purpose of reducing sperm activity which may misalign and unoriented sperm. In such an embodiment the cartridge may be constructed from a thermally conductive material for easily maintaining each reservoir at similar, particularly chilled temperatures.

Sperm Orientation and Alignment

Figure 8:
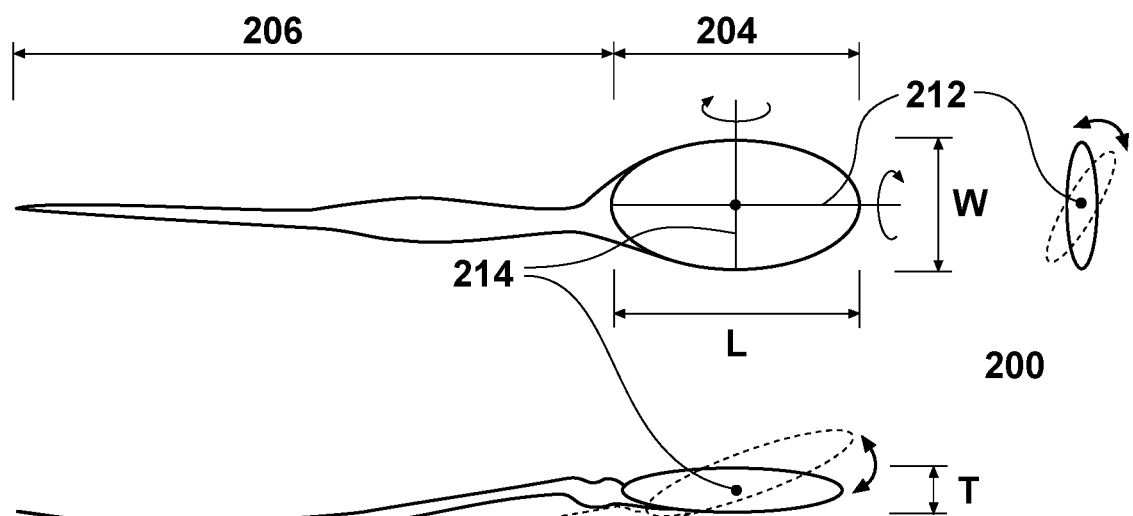
FIG. 8 illustrates a sperm cell having a longitudinal axis.

Referring briefly to FIG. 8 a spermatozoa 200 is illustrated in three views. While some variation exists between species, spermatozoa 200 is representative of the basic shape of a significant portion of mammalian sperm, including bovine sperm, equine sperm, and porcine sperm. The basic sperm head shape may be referred to herein as a generally paddle shaped. As may readily be understood by those of skill in the art the principals described herein will be equally applicable to many other species, such as many of the species listed in *Mammal Species of the World*, by Wilson, D. E. and Reeder, D. M., (Smithsonian Institution Press, 1993), the entire contents of which are incorporated herein by reference.

The two largest portions of the sperm cell 200 are the sperm head 204 and the sperm tail 206. The sperm head 204 houses the nuclear DNA to which DNA selective dyes bind, which is advantageous for the purpose of sex-sorting sperm. The sperm head 204 is generally paddle shaped, and has a greater length than width. A longitudinal axis 212 is illustrated as an axis along the length of the sperm head 204 through its center, which may be generally parallel with the length of the sperm tail 206. A transverse axis 214 is illustrated through the center of the sperm head 204 and perpendicular to the longitudinal axis 212. Relative to an ideal orientation, sperm which is rotated about the longitudinal axis may be considered "rotated" in manner synonymous with the aeronautical term roll, while sperm which is rotated about the transverse axis 214 may be considered "tilted" in a manner synonymous with the aeronautical term pitch. The length of the sperm head is indicated along the longitudinal axis as L. The width of the sperm head 204 is indicated as W, while the thickness is indicated as T. By way of a non-limiting example, bovine of many breeds have sperm dimensions of approximately L=10 microns, W=5 microns, and T=0.5 microns.

Differentiating sperm is difficult in many species because the uptake of DNA selective dye differs only slightly in X-chromosome bearing sperm and Y-chromosome bearing sperm. Most mammalian species demonstrate between about 2% to 5% difference in DNA content. To precisely find this difference each sperm cell analyzed is preferably provided in a uniform alignment and in a uniform orientation. As sperm become unaligned or unoriented their measured fluorescence fluctuates much more than a few percentage points. Ideally, sperm would be aligned in that the longitudinal axis would pass through the focal point of the detector and/or the illumination source while the longitudinal axis and the transverse axis both remain perpendicular to an optical axis of the detector and/or a beam axis of a beam produced by an illumination source. Previous jet-in-air flow cytometers modified for sperm sorting include a side fluorescence detector for the purpose of excluding sperm which is rotated, but side detectors are not present in microfluidic systems, nor does the geometry of current microfluidic chips permit the inclusion of side detectors. The following features may be incorporated individually, or in any combination or permutation in order to provide oriented sperm in a microfluidic chip and/or to determine when sperm are oriented in a microfluidic chip.

Flow Channel Features

Figure 9A:
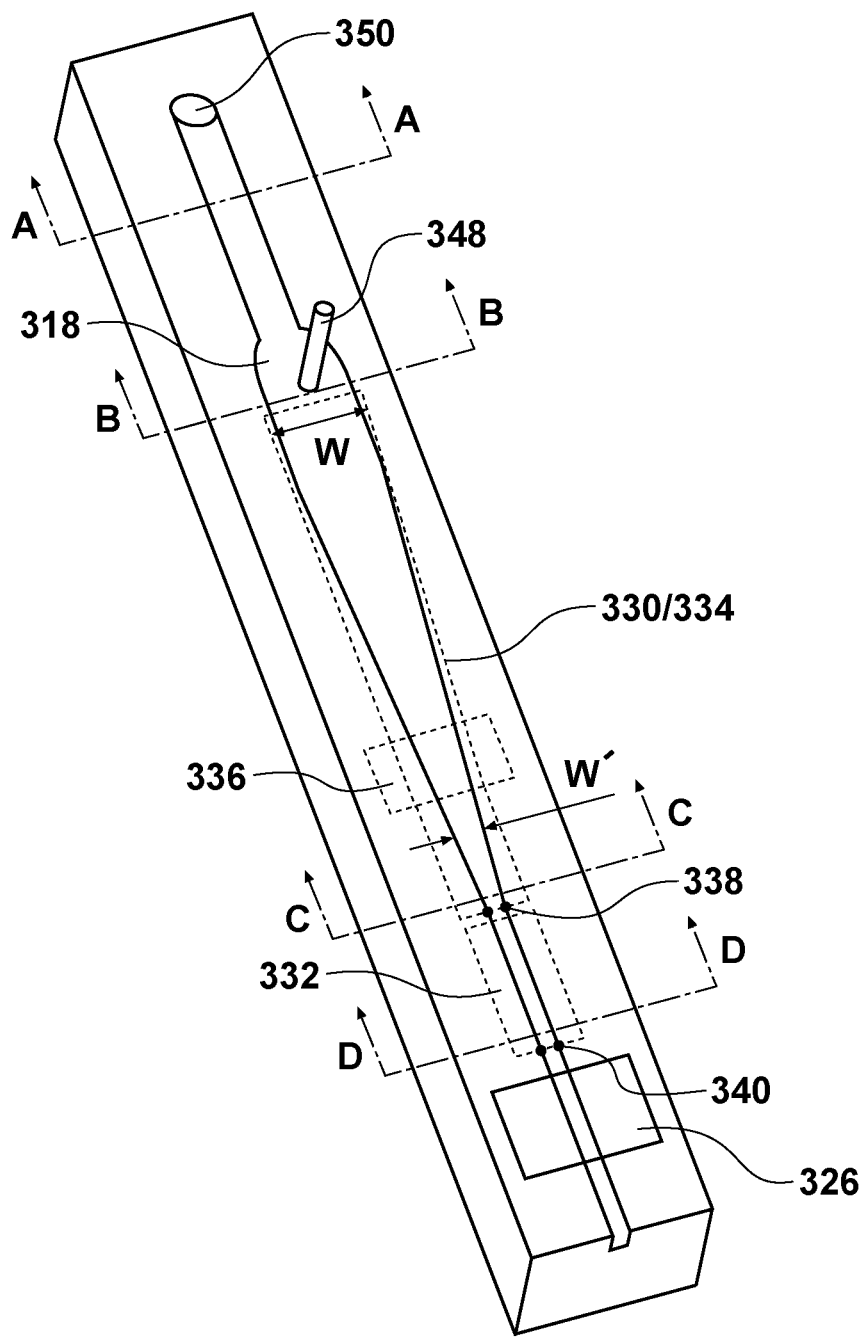
FIGS. 9A-C illustrate a flow channel in accordance with certain embodiments described herein.

Turning now to FIG. 9A, a perspective view of a flow channel 318 is illustrated. The illustrated flow channel 318 includes both a fluid focusing region 330 and a sperm orienting region 332 formed in a portion of a microfluidic chip 300. While the fluid focusing region 330 includes a fluid focusing feature in the form of a fluid focusing geometry and a sperm orienting region 332 is illustrated with the orienting feature of an orienting channel geometry, it should be appreciated other focusing features and orienting features may be incorporated in place of, or in addition to, the depicted geometries.

The flow channel 318 may be one of many flow channels in such a microfluidic chip, such as between 4 and 512 flow channels. A sheath flow inlet 350 is illustrated upstream of the sample inlet 348 in the flow channel 318 for the purpose of establishing the coaxial flow, sometimes referred to as sheath flow.

The fluid focusing region 330 may include a vertical fluid focusing region 336 with a geometry for focusing and/or aligning a vertical aspect of the core stream and a lateral fluid focusing region 334, or transverse focusing region, with a geometry for focusing and/or aligning a lateral aspect of the core stream. As illustrated, the lateral fluid focusing region 334 comprises the same length of the flow channel 318, as the fluid focusing region 330, both of which overlap the vertical fluid focusing region 336. It should be appreciated that the lateral fluid focusing region 334 may occupy less than the entire fluid focusing region, and that the vertical fluid focusing region 336 need not necessarily overlap with lateral fluid focusing region 334. The lateral fluid focusing region 334 may be considered the length of the flow channel 318 along which a lateral channel width "w" decreases ending at a first transition point 338 to a second width "w'". This geometry tends to narrow the core stream of sample, and may generally assist in the aligning sperm cells within the flow channel 318 providing a narrower band of sample in which they are generally confined.

A sperm orienting region 332 may follow the fluid focusing region 330 some distance after the first transition point 338 in the flow channel 318, or alternatively, the fluid focusing region 330 and the sperm orienting regions 332 may overlap partially or entirely. The sperm orienting region 332 may end at a second transition point 340, which may be followed by an inspection region 326. In one embodiment, the channel reduced width "w'" may have a consistent dimension through the sperm orientation region 332, or a portion of the sperm orientation region, and through the inspection region 326.

Figure 9B:
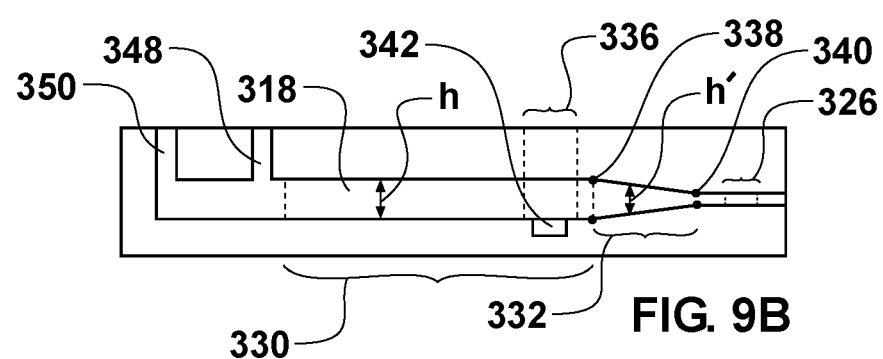

Turning to FIG. 9B, a vertical sectional view of the flow channel 318 is illustrated, having a lateral fluid focusing region 334 and a vertical fluid focusing region 336 followed by an sperm orienting region 332 and an inspection region 326. In one embodiment, the vertical fluid focusing region 336 includes a vertical fluid focusing feature 342, which may be a supplemental sheath channel, a series of lips, edges, chevrons, undulations, or speed bumps, or a transducer capable of producing pressure pulses in the flow channel 318. In one embodiment a channel the height "h" is maintained relatively constant up to the first transition point 338. In other embodiments, the vertical fluid focusing region 336 may have geometry which varies the channel height "h," or the sperm orientation region 332 may overlap with the fluid focusing region 330 introducing a channel geometry which varies the channel height prior to the first transition point 338. In one embodiment, the channel height "h" progresses from the first transition point 338 to a reduced channel height "h'" at the second transition point 340. Alternatively, the channel height "h" may be reduced through the sperm orienting region 332. The sperm orienting region 332 may begin after the fluid focusing region 330, or it may overlap partially, or even entirely with the fluid focusing region 330.

Figure 9C:
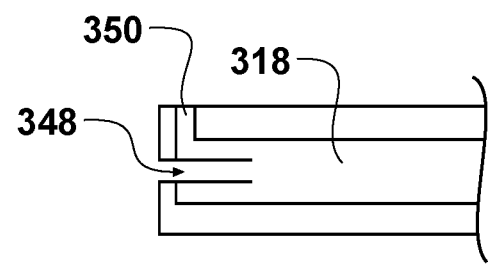

FIG. 9C illustrates an alternative configuration for producing the coaxial, or sheath, flow whereby the sample inlet 348 is provided in generally parallel with the fluid channel 318. In this configuration the sample inlet 348 may be provided in a beveled configuration to encourage a ribbon shape to the core stream at the onset. Those of ordinary skill in the art will appreciate any known configuration for establishing sheath flow in a microfluidic channel may also be incorporated with the orientation aspects described herein. As one non-limiting example, any of the inlet/sample channels described in U.S. Pat. No. 7,311,476, the entire contents of which are incorporated herein by reference, may be incorporated with various features described herein.

FIGS. 10A-D illustrates a flow channel 318 with a relatively simple geometry which incorporate both a fluid focusing region 330 and an sperm orienting region 332; however, each of these regions may also be incorporated into more complex flow channel geometries. Each of FIGS. 10A-D illustrate general principals and are not necessarily depicted to scale or reflect a 1:1 aspect ratio. FIG. 10A illustrates section AA as a generally square flow channel 318 filled with sheath fluid 352. Moving down stream to section BB, FIG. 10B illustrates a core stream of sample 354 is seen in coaxial relationship with the sheath fluid 352. A closer view of the core stream at BB illustrates an example of an unaligned and unoriented sperm cell 360. Arrows around the core stream illustrate the forces applied to the core stream by changes in the flow channel 318 geometry. The transition from AA to BB resulted in a slight widening of the channel without a change in height.

Moving down stream to CC the width "w" of the flow channel 318 is reduced focusing the core stream, which is illustrated at the sperm cell 360 moving to the center of the core stream and becoming aligned, while maintaining an unoriented position in the stream. The forces providing the lateral movement are illustrated as bold arrows emphasizing the hydrodynamic influence of this portion of the channel geometry. From section CC to DD the height "h" of the flow channel is reduced tending to apply orienting forces to sperm within the core stream. Greater forces are applied from vertical positions, as compared to later positions, tending to orient the flat surface of a sperm cell.

FIGS. 11A-11D illustrates a similar flow channel geometry having circular and elliptical cross sections FIGS. 10A-10D, except that the flow channel 318 comprises generally elliptical and circular cross sections.

Core Stream Formation

While a uniform core stream formation is beneficial for many analysis techniques, it is especially useful when differentiating relatively small fluorescence differences from X-chromosome bearing sperm and Y-chromosome bearing sperm. A useful feature of a sperm sorter would be the formation of a core stream having a generally ribbon shape, which may contribute to both sperm alignment and sperm orientation in a flow channel.

Figure 12A:
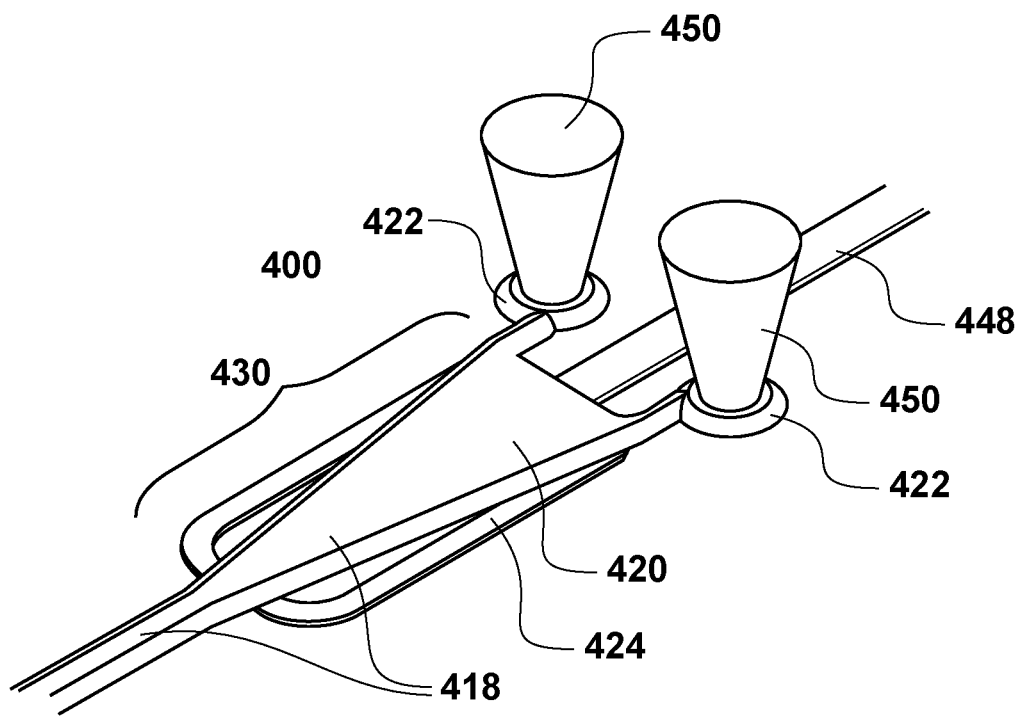
FIGS. 12A-B illustrate a portion of a flow channel geometry in accordance with certain embodiments described herein.

Turning now to FIG. 12A, a fluid focusing region 430 is incorporated into a region of the flow channel 418 for generating core stream flow, or sheath flow. The core stream forming geometry 400 is illustrated as an interior surface of a flow channel 418 in a microfluidic chip 80, such as those microfluidic chips previously described. The core stream forming geometry 400 may be fabricated in plastics, polycarbonate, glass, metals, or other suitable materials using microfabrication, injection molding, stamping, machining, 3D printing or by other suitable fabrication techniques. As such, the core stream forming geometry may be formed in a single layer, or by a plurality of stacked layers.

The illustrated core stream forming geometry 400 provides improved sheath flow capabilities, and thus improved focusing capabilities. In particular, sheath inlets 450 may be provided with conical inlet shapes which are each received at a sheath aggregating volume 422. The sheath aggregating volumes may provide a single outlet, or multiple outlets to further flow channel 418 components. A single outlet is illustrated which extends into the fluid focusing region 430. Alternatively, a single inlet may be branched into the core stream forming geometry 400. Additionally, flow restrictions may be placed on one or more fluidic paths emanating from the sheath aggregating volume 422.

The depicted fluid focusing region 430 comprises a lateral fluid focusing component and a vertical fluid focusing component, both of which contribute to the axial acceleration of both sheath fluid and sample through the flow channel 418. The illustrated lateral fluid focusing component comprises a lateral fluid focusing chamber 420. The lateral fluid focusing chamber 420 is provided with sample from the sample inlet 448, as well as, sheath from one or more sheath inlets 450. As illustrated, two symmetric sheath inlets 450 fill the lateral fluid focusing chamber 420 from the edges, while sample enters the lateral fluid focusing chamber 420 from the middle. As the sample and sheath progress along the lateral fluid focusing chamber 420 the width of the chamber is reduced providing an increasing inwards force from the lateral sides of the chamber which tends to focus the sample in the middle of the lateral fluid focusing chamber 420 and which accelerates both the sheath and the sample in the flow channel. The illustrated vertical fluid focusing component comprises a first vertical fluid focusing channel 424 in combination with the position of the sample inlet 448 relative to the lateral fluid focusing chamber 420. The first vertical fluid focusing channel 424 may comprise a looping channel that branches away from the lateral fluid focusing chamber 420 and is provided in fluid communication with the lateral fluid focusing chamber 420 further downstream. In this manner, the first vertical fluid focusing channel 424 provides a means for diverting a portion of sheath flow that may be reintroduced into the flow channel 418 at a later point to focus the vertical position of the core stream of sample.

Figure 12B:
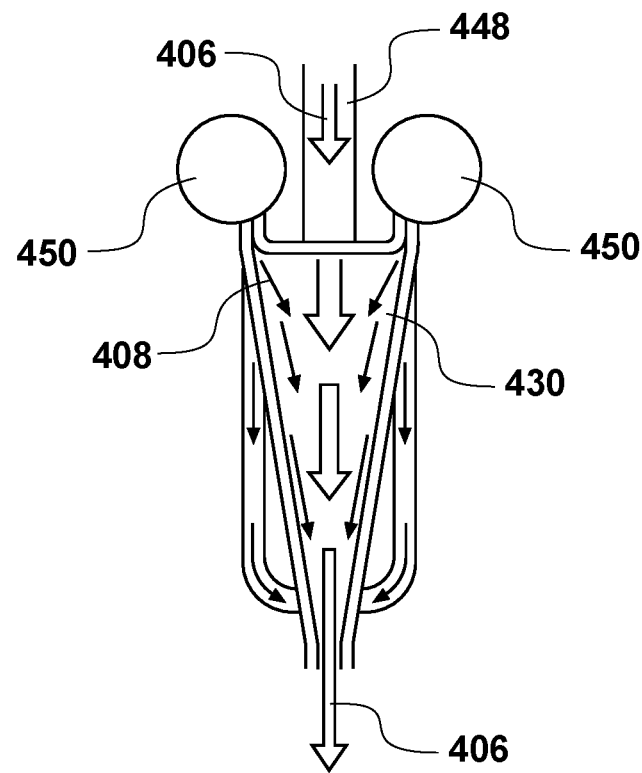

FIG. 12B provides an illustrative view of the lateral fluid focusing component. A sample flow 406 is illustrated entering the lateral focusing chamber 420 from the sample inlet 448. While sheath flow 408 is illustrated entering the lateral fluid focusing chamber 420 from each sheath inlet 450 at the edge of the lateral fluid focusing chamber 420. As the width of the lateral fluid focusing chamber decreases, the sheath flow 408 provides an increasing shearing force on the sample 406, both accelerating the flow of the sample, spacing out particles in the sample, and laterally focusing the sample flow into the center of the lateral fluid focusing chamber 420.

Figure 13:
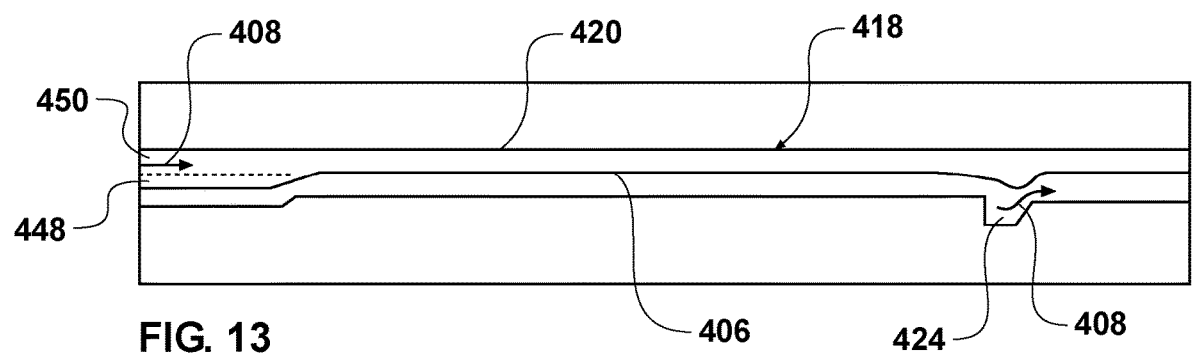
FIG. 13 illustrates a vertical cross section of a flow channel geometry in accordance with certain embodiments described herein.

The vertical flow of the sample 408 is influenced by two features of the core stream forming geometry 400, which can be best seen in FIG. 13. FIG. 13 represents a vertical cross-section along a longitudinal axis of the core stream forming geometry 400. A first downwards vertical influence on the sample stream is created upon entry into the lateral fluid focusing chamber 420, because the sample is introduced from under the lateral fluid focusing region 420, so that its upward flow will be resisted by the sheath flow 408 above it. A representative sample flow 406 is illustrated reaching the end of the sample inlet 448 and moving upwards against a sheath flow 408. Once the core stream of sample 406 reaches the first fluid vertical focusing channel 424, sheath flow 408 directs the sample upwards focusing the sample away from the bottom of the flow channel 418.

Once subjected to the focusing region 430, the sample may continue through a sperm orienting region 330, and an inspection region 326. The sperm may be oriented according to specific features in the following description and a sort action may be performed according to various mechanism described previously.

Figure 14A:
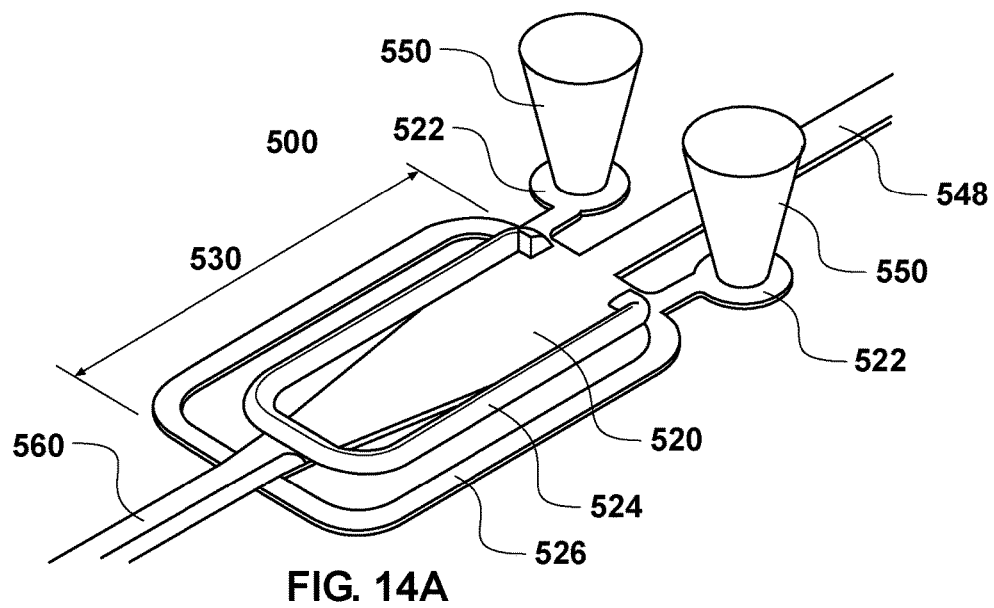
FIGS. 14A-B illustrate a portion of a flow channel geometry in accordance with certain embodiments described herein.

Turning to FIG. 14A, an alternative core stream forming geometry 500 is illustrated which incorporates a fluid focusing region 530 which includes a double horseshoe or double loop in the form of a first and second vertical fluid focusing channels. One embodiment relates to a core stream forming geometry 500 having a first vertical fluid focusing channel 524 and second vertical fluid focusing channel 526 configured contribute opposing vertical fluid focusing sheath flows into a flow channel 518 for an improved core stream formation. FIG. 14A depicts a sample inlet 548 positioned at the same vertical level as the sheath inlet 550 leading in to a lateral fluid focusing chamber 520. The first vertical fluid focusing channel 524 runs vertically above the lateral fluid focusing channel 520 and the second vertical fluid focusing channel 526 runs vertically below the lateral fluid focusing channel 520. After being subjected to the focusing features of the lateral focusing chamber 520, the first vertical focusing channel 524 and the second vertical focusing channel 526, a more focused and/or aligned core stream may flow through the remainder of the flow channel 560.

Figure 14B:
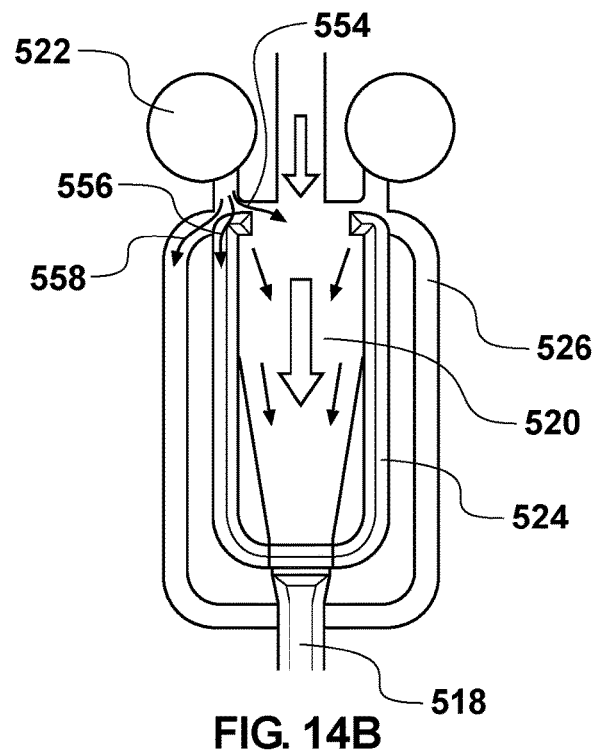

Referring to FIG. 14B, sheath flow is illustrated through the sheath inlet and divided into three parts. A first sheath flow 554 enters the lateral fluid focusing chamber 520, and in response to the narrowing width tends to focus the sample in the center of the lateral fluid focusing channel 520. A second portion of sheath flow 556 is diverted through the first vertical fluid focusing channel 524 and a third portion of sheath flow 558 is directed through the second vertical fluid focusing channel 526. A sheath aggregating volume 522 which provides a greater cross sectional area than the end of the conical sheath inlet 550 provides a beneficial volume for distributing relatively high sheath flow rates through each of the sheath portions. In particular increased sheath flow through the first vertical focusing channel 524 and the second vertical focusing channel 526 may provide for an improved ability to focus the vertical position of a core stream in a flow channel 518.

Figure 15:
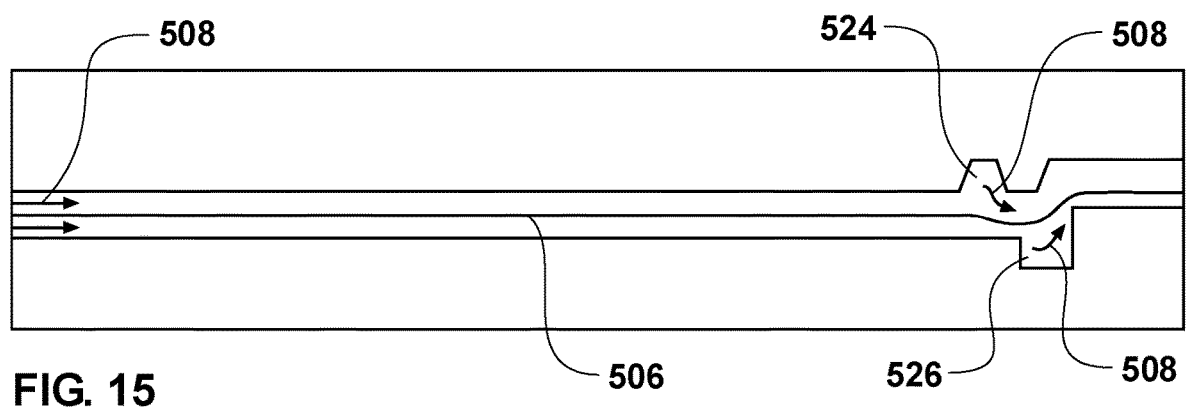
FIG. 15 illustrates a vertical cross section of a flow channel geometry in accordance with certain embodiments described herein.

Turning now to FIG. 15, a vertical cross-section along a longitudinal axis of the core stream forming geometry 500 illustrates a core stream of sample 506 and a sheath fluid 508 introduced into the flow channel 518 at substantially the same vertical position. Sheath flow 508 from the first vertical fluid focusing channel 524 provides a downward focusing influence on the core stream of sample, followed by an upward focusing influence from sheath fluid provided from the second vertical fluid focusing channel 526. The portion of the flow channel 518 following the opposing vertical sheath flows is at an elevated vertical position relative to the lateral fluid focusing chamber 520 and the sample inlet 548. The portion of the flow channel 518 following the focusing region may then be manipulated in a region design to impart orientation to particles in the core stream of sample.

Figure 16:
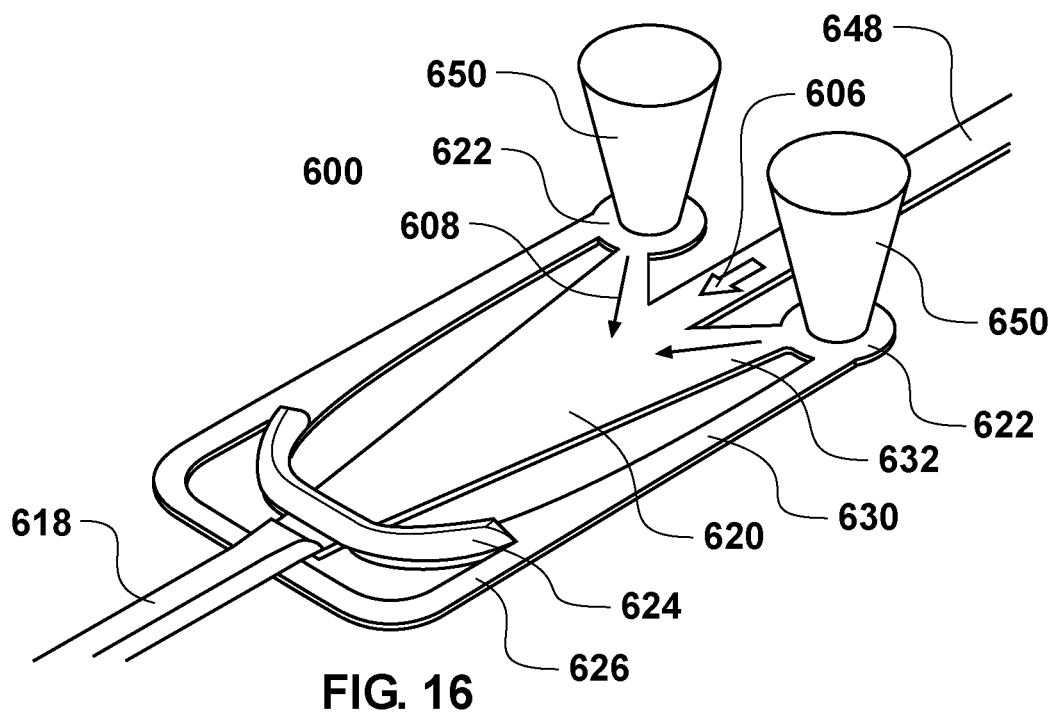
FIG. 16 illustrates a portion of a flow channel geometry in accordance with certain embodiments described herein.

FIG. 16 illustrates an alternative embodiment of the core stream forming geometry 600, which presents substantially the same vertical cross section depicted in FIG. 15. There may be certain efficiencies gained in several stream lined aspects relating to the sheath fluid flow paths illustrated in FIG. 16. In one aspect sheath fluid passes through from the each sheath aggregating volume 622 into focused inlet 632 which immediately puts the sheath fluid into a trajectory for laterally focusing the core stream of sample fluid 606. Each of the first vertical fluid focusing channel 624 and the second vertical fluid focusing channel 626 are also streamline with a common inlet 630.

Figure 17:
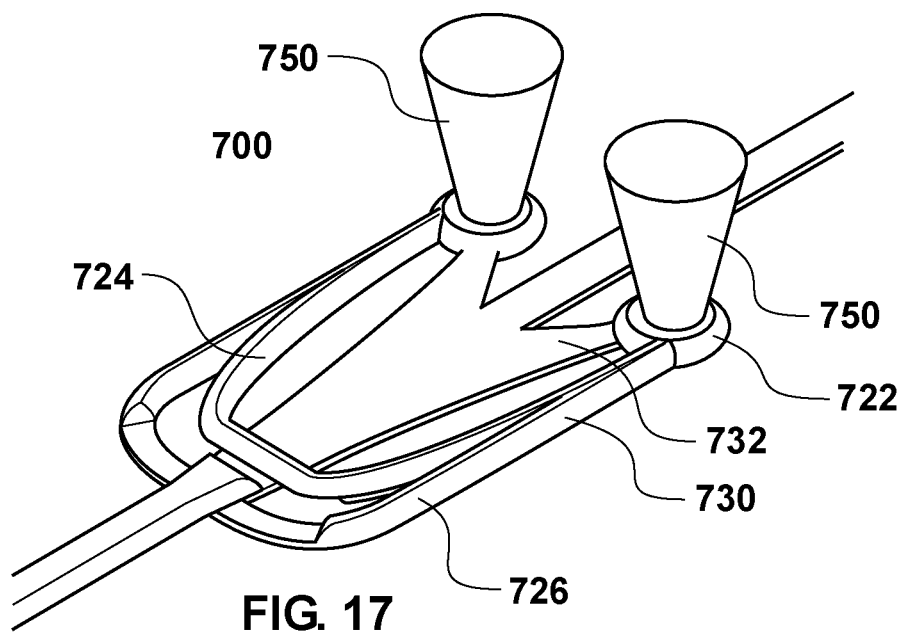
FIG. 17 illustrates a portion of a flow channel geometry in accordance with certain embodiments described herein.

FIG. 17 illustrates another embodiment of the core stream forming geometry 700, having streamlined sheath flow components, such as a narrow inlet 732 and the common inlet 730 connected directly to the sheath aggregating volume 722 of each sheath inlet 750. Additionally, FIG. 17 illustrates an alternative vertical placement of some portions of each of the first vertical fluid focusing channel 724 and the second vertical fluid focusing channel 726.

Orientation with a Planar Flow Channel

Figure 18A:
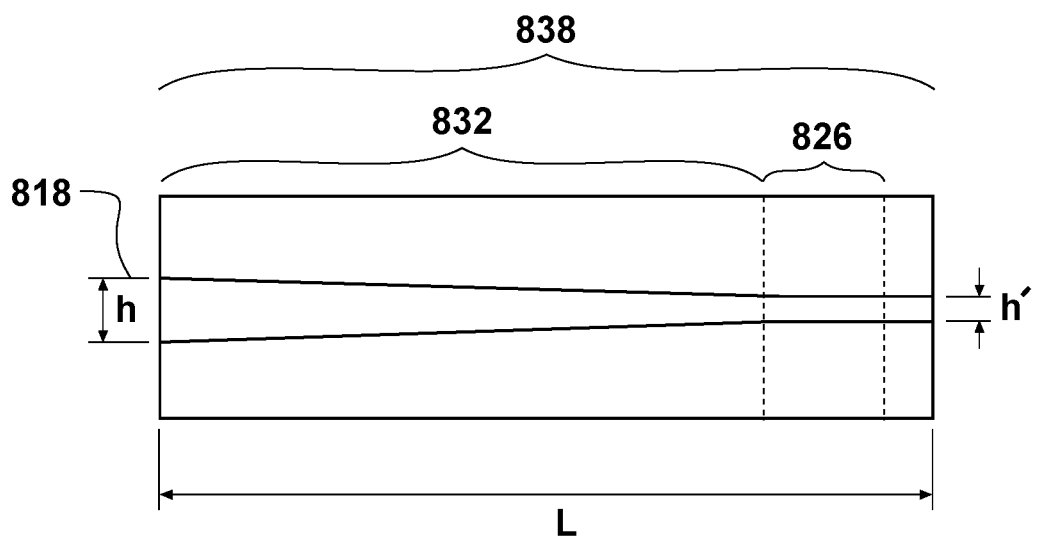
FIGS. 18A-C illustrate an orienting geometry in accordance with certain embodiments described herein.

Turning to FIG. 18A, one embodiment of an orienting channel geometry is illustrated whereby the flow channel 818 transitions to a reduced height, which may generally be referred to as a planar orienting geometry 838. Such an orienting geometry may encompass both an orientation region 832 and an inspection region 826. The planar orienting geometry may follow any of the above described fluid focusing geometries or features, such as any one of the described core stream forming geometries.

Prior to the planar orienting channel geometry 832, the flow channel 818 may have a height between about 25 microns and 75 microns and a width between about 100 microns and about 300 microns. The height "h" prior to the orienting channel geometry 832 may be reduced to a second height "h'" over a length L. The reduced height "h'" may be between about 10 microns and 35 microns for producing a core stream which approaches 1 to 0.5 microns in the narrow axis, or which approaches the thickness of a sperm cell. FIG. 18A illustrates a gradual transition where the length of the transition "L" may be between about 200 microns and about 5000 microns. Prior to the transition the flow channel 818 may have a width to height ratio between about 4:1 and 5:1, and after the transition the width to height ratio may be about 8:1 and 10:1.

Figure 18B:
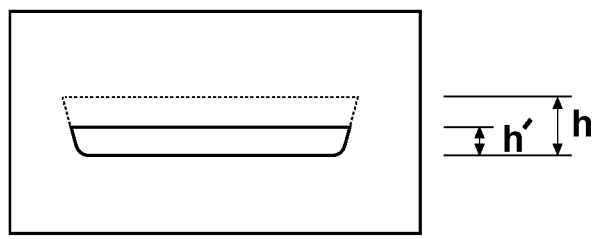

Immediately following any focusing geometry, the flow channel 818 may have a generally rectangular shape, or to adjacent edges may be rounded resulting in a "D" shaped profile, seen in the transverse sectional of FIG. 18B. The beginning profile is indicated in hidden lines providing a comparison of the two profiles.

Figure 18C:
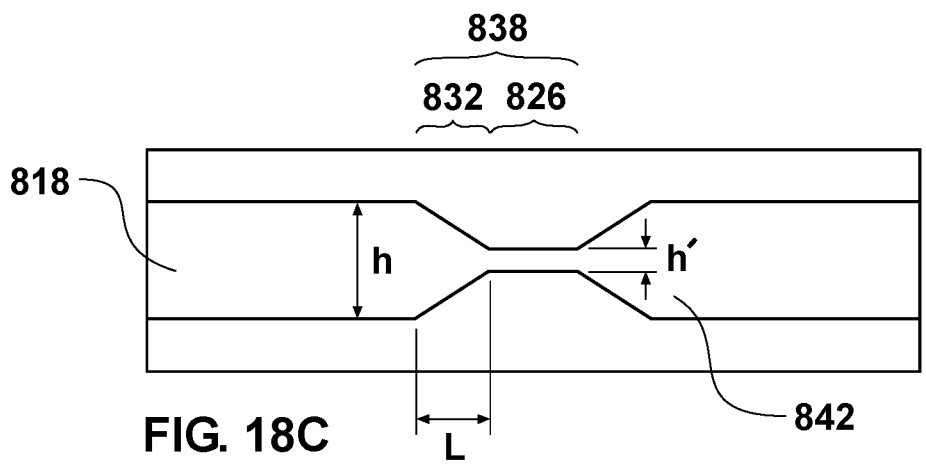

FIG. 18C illustrates a sudden transition right before the inspection region 826, which may have a transition length "L" between about 25 microns and about 200 microns. In one embodiment, there may be a re-expansion 842 immediately following the inspection region 826. The combination of the short transition and the re-expansion may provide for a system which requires less pressure to drive cells though, or which reduces the back pressure of the system.

Orientation in a Nozzle Mimicking Geometry

Figure 19A:
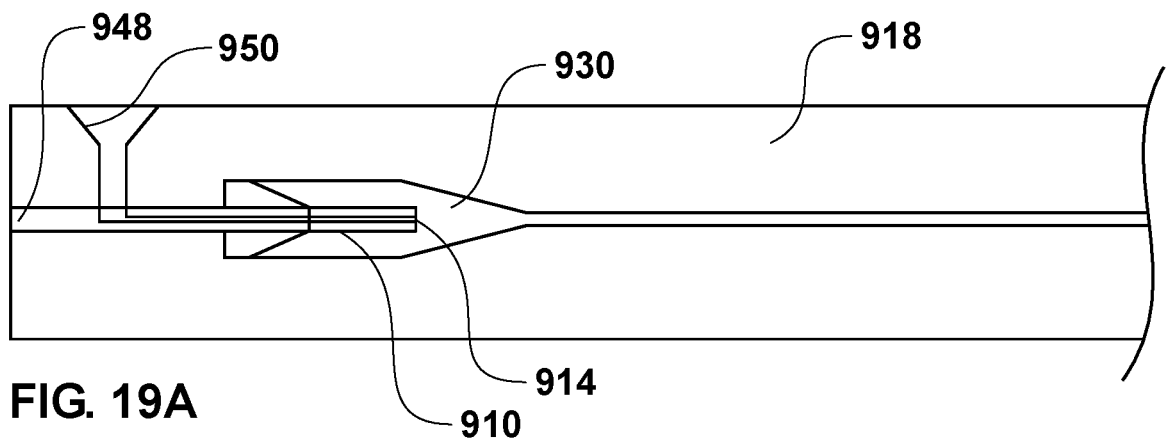
FIGS. 19A-C illustrate an orienting geometry in accordance with certain embodiments described herein.
Figure 19B:
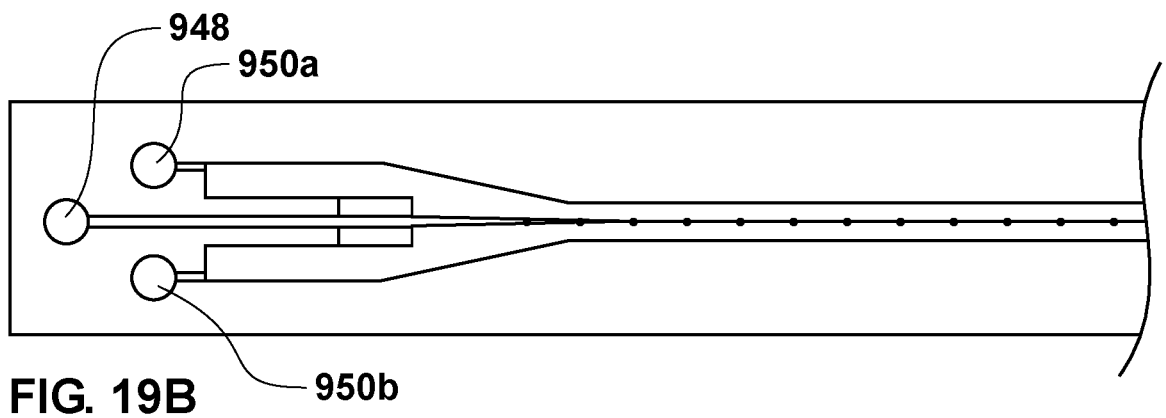
Figure 19C:
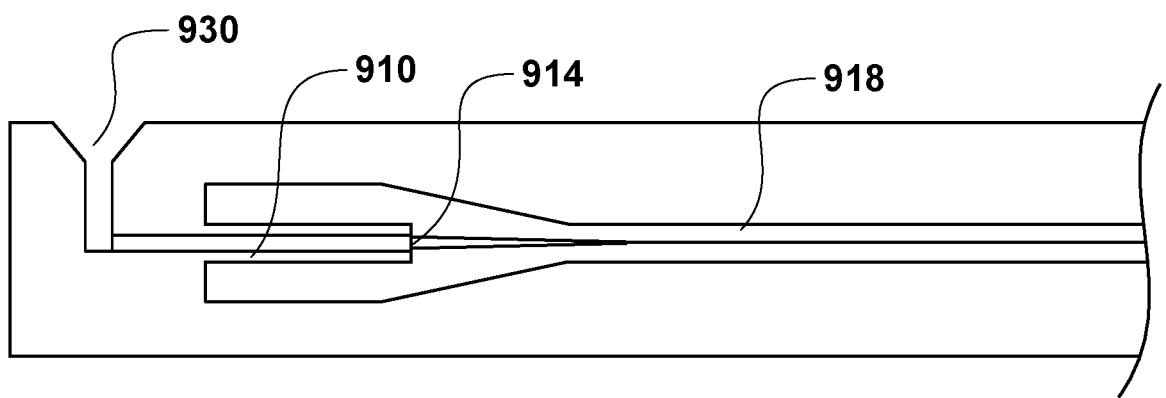

With reference to FIGS. 19A-19C, one embodiment of a flow channel 918 is provided with an orienting geometry that mimics an orienting nozzle of a jet-in-air flow cytometer. In such an embodiment, the fluid focusing features and the sperm orienting features may overlap and in fact be incorporated into a common geometry. A flow channel 918 is provided in fluid communication with a first sheath inlet 950a and a second sheath inlet 950b, each of which feed into an orienting chamber 930. The orienting chamber 930 may comprise an internal surface area which mimics the interior of a nozzle. A sample inlet 948 is fed through an injection tube 910 through an injection tube outlet 914 into the orienting chamber 930. The orienting chamber 930 may have a generally elliptical cross-section at its most upstream point, but it also may be circular or rectangular. Regardless of the height of the orientation chamber may be about 1000 microns. The interior surface of the orienting chamber may transition over 5000 microns to a generally elliptical, or even a "D" shaped channel having a height of 50 microns and a width of 200 microns. The injection tube 910, may extend about 3000 microns into the orienting chamber and may have one or both or internal and external features provide a ribbon core stream and orienting particles, such as sperm, within the core stream. As one example, the injection tube may have a beveled tip. As another example, the injection tube may have an elliptical or even rectangular internal channel ending at the injection tube outlet. The injection tube 910 may have an external thickness of about 300 microns. As a non-limiting example the internal channel may have a height of about 100 microns and a width of about 200 microns.

Downstream Channel Features

Various downstream features may be incorporated into a flow channel in combination with any of the orienting or focusing features previously discussed. Such features may provide a biasing force which tends to orient or align particles. In one embodiment, downstream channel features may be the primary, or even the only, sperm orienting features in a flow channel. In such an embodiment, downstream channel features provide sufficient orientation for anyalsis and sorting. In another embodiment, the downstream channel features are used in combination with other focusing features and/or orienting features and may serve to realign or reoriented sperm which has started to become unaligned or unoriented, respectively. The downstream channel features may also be provided just prior to an inspection region for the purpose of obtaining optimum effectiveness in orienting particles, such as sperm cells.

Figure 20A:
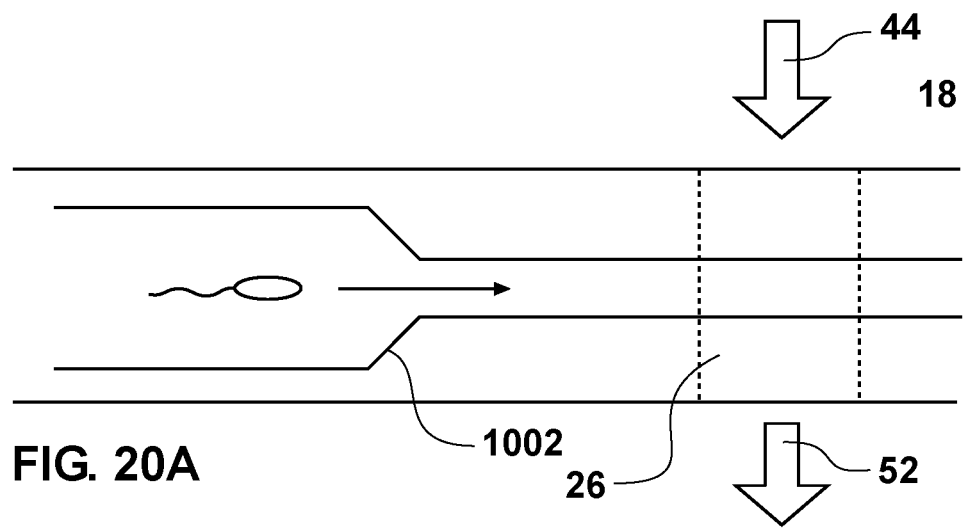
FIGS. 20A-D illustrate flow channel features in accordance with certain embodiments described herein.

Turning to FIG. 20A, a downstream channel feature is illustrated in the form of a ramp 1002, which may be in a portion of a flow channel 1018. The ramp 1002 may present a relatively abrupt reduction in the height of the flow channel, as described with respect to FIGS. 18A-C. The ramp 1002 may be designed in order to present a core stream which has a thickness only slightly larger than the thickness of a sperm cell. A ramp 1002 having an incline less than 45 degrees may be considered a gently ramp, whereas a ramp having an incline between 45 degrees and 90 degrees may be considered an abrupt ramp.

FIG. 20A provides an example of an excitation region 26 which overlaps with the downstream channel feature. The ramp 1002 is illustrated on at least two surfaces on the interior of the flow channel, and may end shortly after the inspection region 26 in order to reduce backpressure and to allow fluid to flow more easily through the system.

Figure 20B:
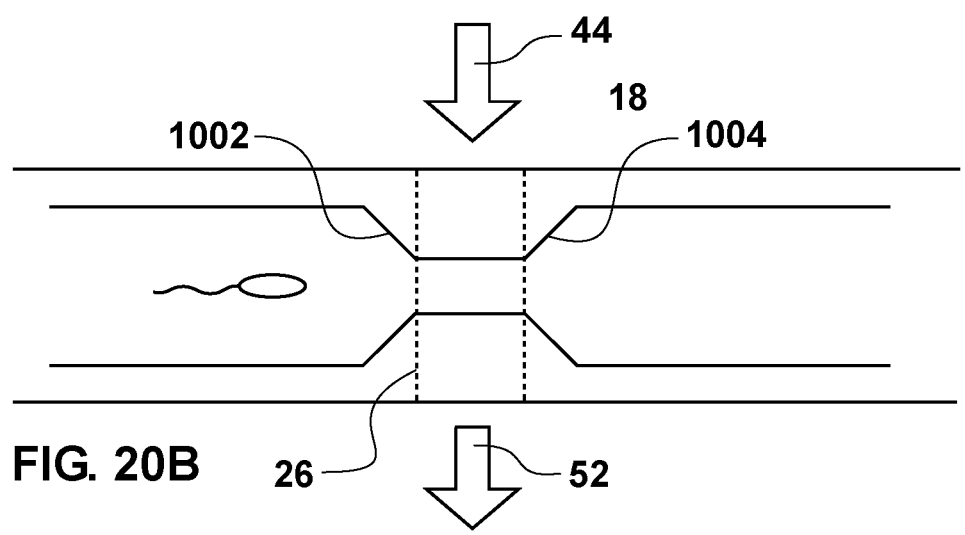

FIG. 20B provides a downstream channel feature in the form of a ramp 1002 followed by an expansion 1004, which may be called a speed bumps. These speed bumps may be placed in series to focus a core stream just prior to the inspection region as well as for orienting sperm in the core stream. In one embodiment, speed bumps or series of speed bumps are present on single surface of the flow channel 18, while in another embodiment speed bumps or series of speed bumps may be present on more than one surface of the flow channel 18. In a related embodiment, a single speed bump may have rounded edges and may be referred to as an undulation. Similarly, a series of rounded speed bumps may be referred to as a series of undulations. An undulation or a series of undulations may be present on a single surface, or may be present on multiple surfaces in a flow channel 18. The speed bumps and/or undulations may extend between about 5 microns and 15 microns into the flow channel 18.

Figure 20C:
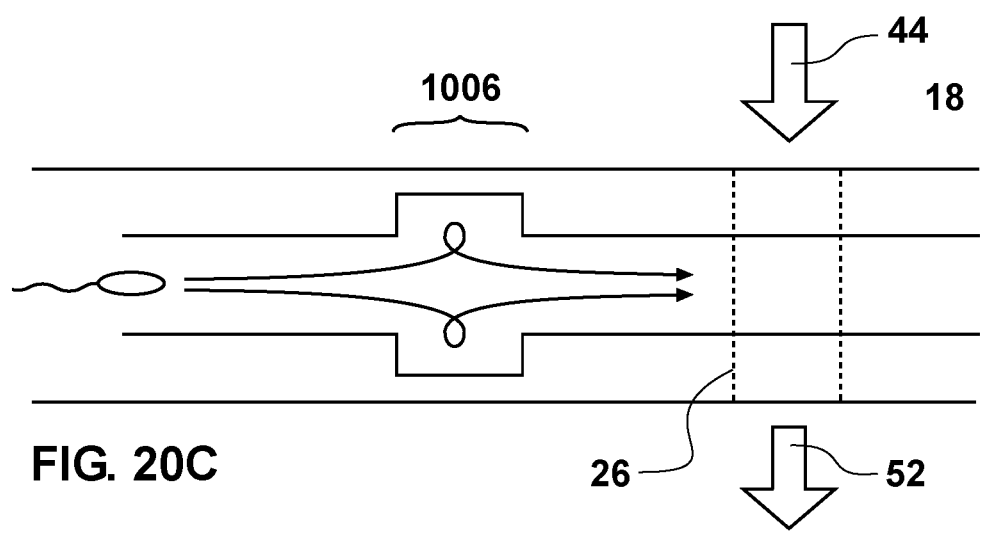

FIG. 20C illustrates a downstream channel feature in the form of a decompression-compression zone 1006, which may also be considered an inverse speed bump. Flow is illustrated entering the zone where it initially disperses at the widening of the channel. As the flow continues, it is recompressed at the abrupt end of the widened region. While the depicted embodiment provides for edges, the surfaces may be smooth resulting in another embodiment of undulations. These features may extend between about 5 microns and 15 microns into the flow channel.

Figure 20D:
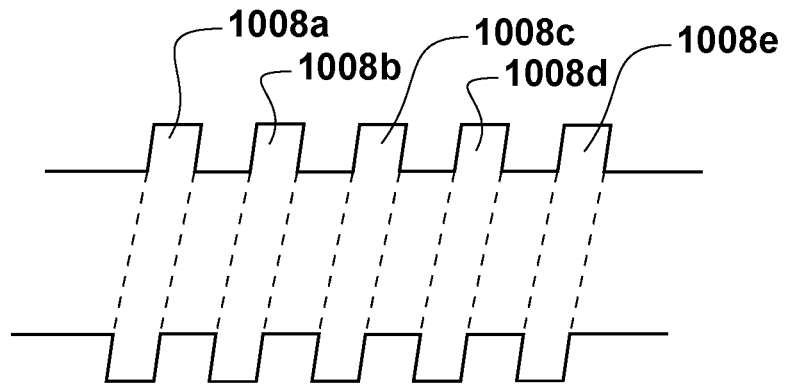

FIG. 20D illustrates a series of chevron shaped features 1008 which may be placed in the flow channel 18. The series of chevron shaped features 1008 provide series of forces which may tended to focus the core stream. The chevron shaped features 1008 may comprise a cut away feature on three sides of a flow channels. In one embodiment the chevron shaped features 1008 may be tilted or slanted. The chevron shaped features 1008 may also have rounded edges for subjecting the core stream to a series of undulations. Like the reverse speed bumps, the cheverons may extend between about 5 microns and 15 microns into the flow channel 18.

Sperm Alignment/Orientation with Magnets

Figure 21A:
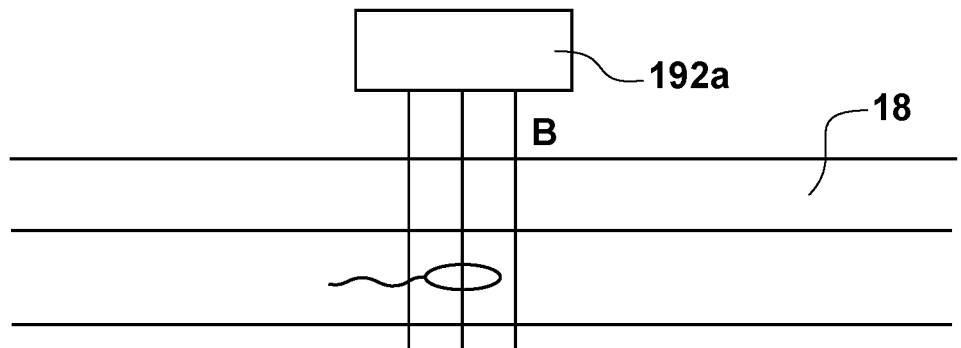
FIGS. 21A-B illustrate alternative embodiments of sperm orienting features in accordance with certain embodiments described herein.
Figure 21B:
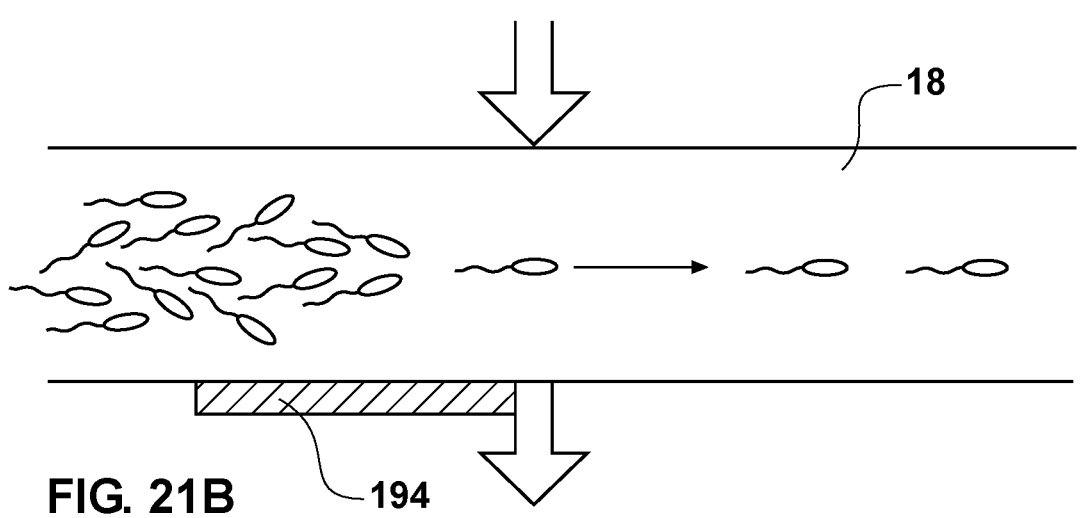

Turning to FIG. 21A, an embodiment of sperm orienting features are depicted as a first magnet 192A and a second magnet 192B which are utilized to provide a magnetic field B to the desired orientation of sperm cells. The first magnet 192A may be located in a vertical position above a flow channel and the second magnet 192B may be located in parallel below the flow channel to produce a static magnetic field B which acts upon sperm moving through the flow channel. The magnets may be placed in other orientations so long as the magnetic field is perpendicular to the sperm cells, which have been shown to align with their planar dimension perpendicular to the applied field. In certain embodiments, it may be desirable to produce a magnetic field strong enough to orient sperm in as many as 512 channels. One or more series of magnets may be used in combination to produce this static magnetic field. In one non-limiting embodiment, the magnets 192 may be arranged to generate a field between about 0.05 Tesla to about 1.0 Tesla.

Sperm Alignment/Orientation with Transducers

In an alternative embodiment, a transducer or a series of transducers may be placed across one or more flow channels on the exterior of a microfluidic chip. An example of a transducer may be a piezoelectric transducer having a generally planar surface 194 in contact with an exterior surface of the microfluidic chip. Said transducers may be driven to produce a standing wave in the flow channel. Sperm may be driven to nodes and antinodes of the standing wave resulting in both an alignment, and possible orientation of sperm in the flow channel.

In some embodiments, a standing wave may be produced with a planar transducer in addition to other orienting or aligning features. For example, the a standing wave may be produced in the flow channel for the purpose of spacing and aligning sperm, while a magnetic field may be applied to the flow channel to orient sperm. As a non-limiting example, it has been surprisingly found a planer transducer operating between 10-16 MHz may improve sperm orientation while flowing in a flow channel.

Measuring Sperm Properties

Regardless of the orienting and focusing features employed in each flow channel a great deal of precision is required in illuminating sperm and detecting emitted or reflected electromagnetic radiation from illuminated sperm. Sperm are living, motile cells which may be erratically propelled by motion from their tail. As such, even with great care in aligning and orienting sperm in a flow channel, there always exists the potential for a number of sperm to become unoriented or to resists orientation forces altogether. Previous efforts may have considered the possibility of illuminating sperm head on, or from all sides. However, such configurations are inapplicable to multiple flow channels in a single chip as each channel requires a considerable amount of space for both collection optics and illumination optics, including reflective surface and/or refractive lenses.

Illumination

In previous jet-in-air flow cytometers, each nozzle or stream tends to be monitored separately for performance and sort characteristics. However, in a microfluidic chip having 4 to 512 flow channels it is desirable to pool certain data for data tracking and display purposes. Because the variation in fluorescence produced in stained sperm is minimal, variations in the illumination of each the flow channels should be reduced or eliminated. A system like that described in U.S. Pat. No. 7,492,522, the entire contents of which are incorporated herein by reference, may be employed for providing uniform illumination across a plurality of flow channels 18.

Referring briefly back to FIG. 1, an electromagnetic radiation source 30 is illustrated which may be a quasi-continuous wave laser such as a Vanguard 355-350 or a Vanguard 355-2500 model laser available from Newport Spectra Physics (Irvine, Calif.). Electromagnetic radiation 46 emitted from the electromagnetic radiation source 30 may be manipulated by beam shaping optics 40 and/or a beam splitting device 74 in free space to produce one or more manipulated beam(s) 44, sometimes referred to as beam segments or beamlets. These beamlets may take the form of one or more beams altered to provide uniform intensity, power, and/or geometry to a plurality of flow channels.

A configuration to achieve uniform beam segments may include beam shaping optics 40 in free space for shaping electromagnetic radiation from the electromagnetic radiation source 30 into a highly uniform profile in one or more axes, such as a "top-hat" or "flat top" beam profile. As but one example, the beam profile may have a uniform intensity in one or more axes or may have a Gaussian intensity distribution in one or more axes. In one embodiment a top-hat profile beam may be split into multiple beam segments according to the number of flow channels in the microfluidic chip. A segmented mirror, or another device for spatially separating segments of the beam, may follow the initial beam shaping optics for projecting multiple beam segments on the flow channels of the fluidic chip. The resulting beam segments may be substantially parallel and spaced according to the spacing of the flow channels.

In an alternative embodiment, the beam shaping optics may provide the beam with a final beam intensity profile, and the beam intensity may subsequently be divided by beam splitting mirrors or other suitable optical beam splitting devices, into multiple beams, or beam segments having uniform dimensions. As one example, an array of beam splitting mirrors, such as micro array of beam splitting mirrors may be employed. In a chip that approaches 256 to 512 flow channels, a combination of beam splitting elements may be used. For example a beam may be split into several beam segments, for example four to eight, by conventional beam splitting mirrors such that the original beam profile is maintained in each beam segment at a fraction of the original beam intensity. Each beam segment, once so formed, may be split by a segmented mirror to illuminate each flow channel in the microfluidic chip.

Additionally, in an alternative embodiment, blocking or masking elements may be placed in the beam path of each beam segment. The blocking or masking elements may be unique to each flow path, or may be shaped to help ascertain specific information regarding particle velocity in the flow path, particle alignment in the flow path, or even particle orientation in the flow path. Such elements may be located in free space or may be incorporated on the substrate of a microfluidic chip 80.

Detection

Figure 22:
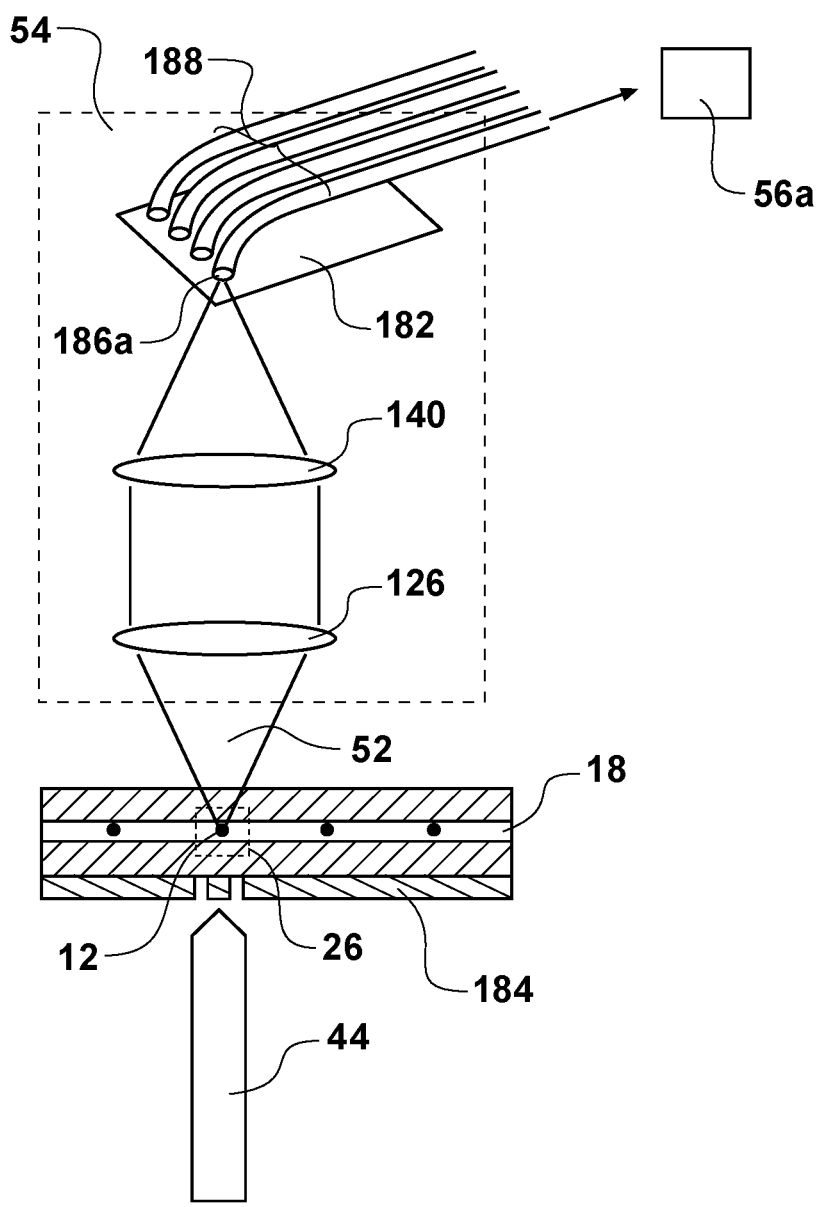
FIG. 22 illustrates collection optics in accordance with certain embodiments described herein.

Referring now to FIG. 22, an example of collection optics 54, or a portion of the collection optics, is illustrated for use in various systems described herein. A representative manipulated beam of electromagnetic radiation 44 may be incident upon the inspection zone 26 of the microfluidic chip 80 at a direction normal to the flow channel. Emitted electromagnetic radiation 52 in the form of forward fluorescence is illustrated emanating from the particle, which may be a sperm cell 12.

The collection optics 54 may be placed in the beam path of the manipulated beam of electromagnetic radiation, or at 0 degree position with respect to the excitation beam 44. The collection optics 54 may include a high numerical aperture collection lens 126 for the focused collection of reflected and/or emitted light in the inspection region 26 of each flow channel 18. An objective lens 140, or multiple objective lenses, may focus the collected emitted and/or reflected light onto an image plane 182 that is incident on a surface mounting an array of fiber optic cables 188 having a fiber optic cable 186 configured for an inspection region 26 of each flow channel 18. In one embodiment, the objective lens 140 may comprise a large objective lens or a series of lens capable of fluorescence emissions from a large chip area onto a plurality of respective detectors, or fibers in communication with detectors. As a non-limiting example, the collection optics 54 may comprise a large area, low f-number optical system configured to collect from an area having a length or width between about 25 mm and 75 mm and having an f-number within a range of about 0.9 and 1.2 and configured for a working distance of about 10 mm and 30 mm. Alternatively, one or more microlenses or microlens arrays could also be used to collect emitted fluorescence from multiple flow channels.

Figure 23:
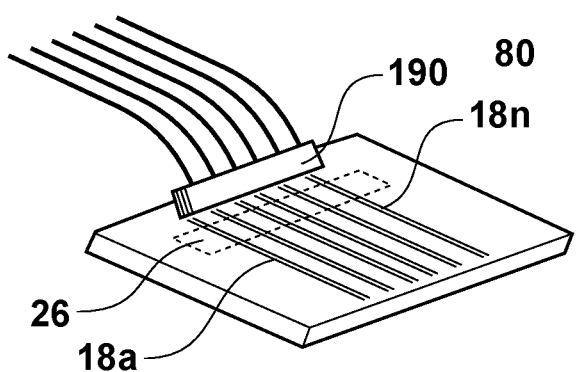
FIG. 23 illustrates an array of detectors in accordance with certain embodiments described herein.

FIG. 23 illustrates an optical arrangement 190, such as an array of fiber optic cables that may be used for capturing forward or side fluorescence from a series of parallel flow channels 18 in a microfluidic chip 80. Such an optical arrangement may be used for the collection of side fluorescence in addition to the collection optics of FIG. 22. Alternatively, the optical arrangement 190 may be positioned in the forward position, or at 0 degrees, to directly collect forward fluorescence from each flow channel 18. In an illustrative embodiment, each first detector in the array of first detectors and each second detector in an array of second detectors may be side fluorescence detectors. In sperm sorting operations, these detectors may function to determine when sperm or unoriented, whether they are unoriented due to rotation, or due to tilt.

Figure 24A:
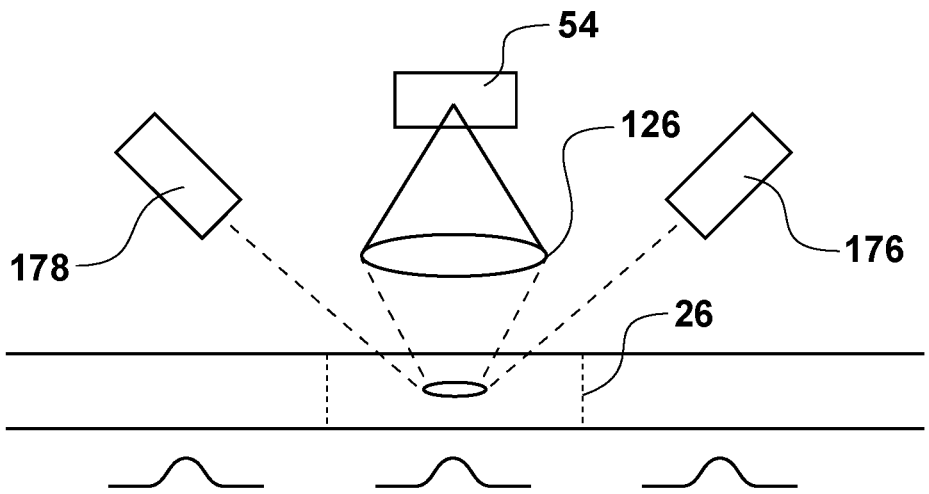
FIGS. 24A-E illustrate various detection schemes in accordance with certain embodiments described herein.

FIG. 24A provides an example of a detection scheme incorporating the collection optics 54 for detecting a forward fluorescence in addition to a first side detector 176 collecting side fluorescence at about a 45 degree angle and a second side detector 178 collecting side fluorescence at 45 degrees in the opposite direction. The first side detector 176 and the second side detector 178 may be characterized as having a 90 degree angle between the optical axis of each.

In addition to the schematic of the detection scheme illustrated in FIG. 24A, FIGS. 24A-E, provide various sperm orientations within a flow channel 18, in addition to the waveform pulses that may be generated by each of the forward detector 54, the first side detector 176 and the second side detector 178 associated with the inspection region 26 of each flow channel. These waveform pulses may be determined in the analyzer, and characteristics or features of the waveform pulses may be calculated for use in a sorting logic applied by the analyzer 58. Generally, it should be appreciated that a detector with an optical axis normal to the flat paddle shaped surface of sperm will provide the maximum possible signal, while a detector than an optical axis which is parallel to the planar surface will effectively be looking at the narrow edge of a sperm head and may generate a significantly lower signal.

FIG. 24A provides an example of a sperm cell 12 in a flow channel without rotation or tilt, allowing the forward fluorescence signal to capture a maximum pulse height and pulse area for direct comparison to other waveform pulses representing other sperm cells. The waveform pulses generated by the first side detector 176 and the second side detector 178 can be seen as substantially similar to each other.

Figure 24B:
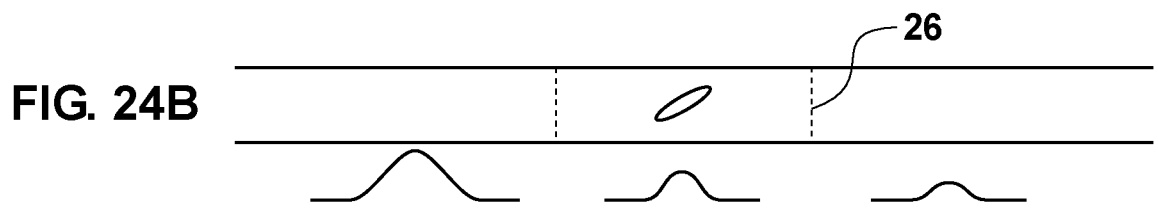

Turning to FIG. 24B a tilted sperm cell 12 has about a 45 degree downward tilt presenting the first side detector 176 within a normal fluorescence and presenting the second side detector 178 with the edge of the sperm. Under certain circumstance the edge of the sperm may fluoresce very brightly, but more briefly that it would in other orientations. The waveform pulse produced by the first side detector 176 will have a, peak height, peak area, and peak width which may be compared to the waveform pulse produced by the second side detector 178, as well as the waveform pulse produced from the forward detector 54.

Figure 24C:
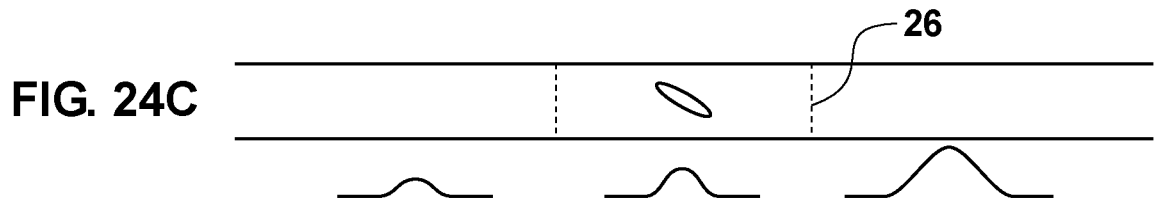

Similarly, FIG. 24C provides an example of a sperm head which is tilted upwards 45 degrees presenting the first side detector 176 with one fluorescence and the second side detector 178 with a normal fluorescence. Again a significant difference may exist in the pulse height, pulse width and pulse area of the resulting waveform pulses from the side detectors. Thus, measured waveform pulse parameters may be analyzed to determine when sperm cells are tilted during detection. Differences in waveform pulse height, area, width, may be compared to determine disparities. When disparities exceed a threshold, it may be determined a sperm cell was not aligned well enough to accurately differentiate the presence of X-chromosome bearing sperm or Y-chromosome bearing sperm. Additional parameters may also be determined for comparison, such as a pulse slope, rise time, and inner pulse area.

Figure 24D:
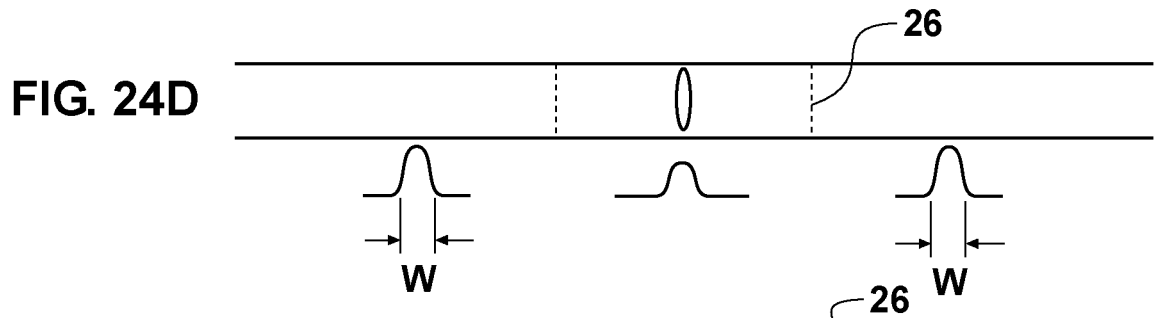

FIG. 24D illustrates a sperm cell which is tilted 90 degrees. In this event, the waveform pulses produced by the first side detector and the second side detector may be very similar. The waveform pulse produced by the forward detector should vary drastically, for example the pulse width, rise time and area may be distinguishable from sperm in a proper orientation.

Figure 24E:
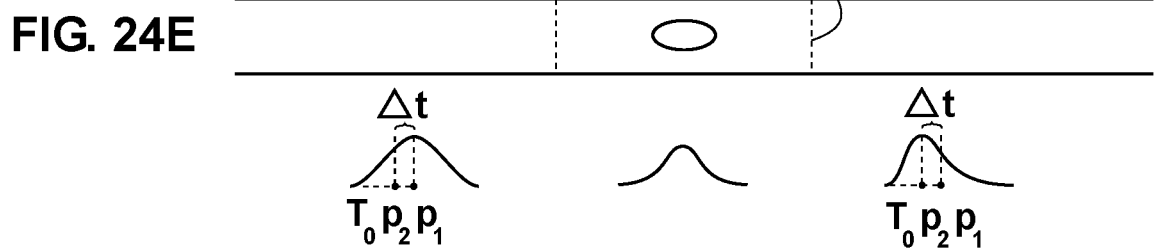

FIG. 24E illustrates a sperm cell which is rotated about its longitudinal axis. The curvature of a sperm head may provide the first side detector and the second side detector with similar signals, but an offset or lag may exist between the times each waveform peaks. Therefore, a rise time, slope or peak lag may be calculated between the two signals to determine when cells.

In many embodiments described herein features and geometries are employed that attempt to orient sperm for both tilt and rotation. However, some percentage of sperm will fail to become oriented regardless. Despite the described orienting features, some sperm may be sent into a tumbling state within the flow channel. Such sperm might exhibit a high propensity to become unoriented in terms of tilt and rotation. Therefore, while rotation itself may be more difficult to detect in a microfluidic chip, any described means for detecting tilt may also aid in eliminating rotated sperm from gating for sex sorting.

As can easily be understood from the foregoing, a true side fluorescence value, or alternatively side scatter, have not been measured in multiple flow channels of a microfluidic chip previously. In the field of sperm sorting, such a measured side fluorescence would provide valuable information regarding sperm orientation.

Figure 25A:
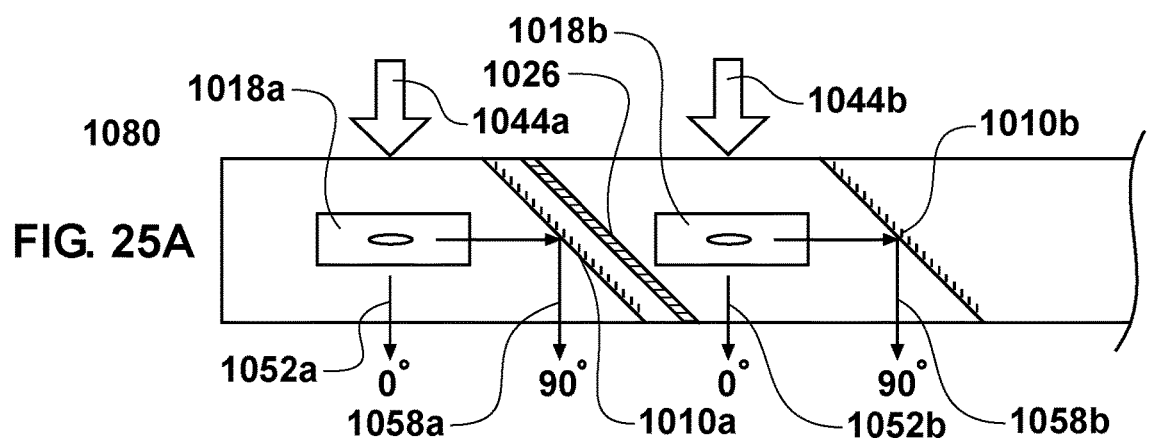

FIG. 25A illustrates a microfluidic chip 1080 configuration providing the ability to measure both forward fluorescence 1052 and a side fluorescence 1058 in a flow channel 1018, or in each of multiple flow channels. A cross sectional view of a portion of a microfluidic chip 1080 is provided whereby flow in the flow channel 1018 may be understood to be in the outward direction. The dimensions of the flow channel 1018 may be overemphasized for clarity.

A reflective element, in the form of a reflective surface 1010 may be associated with each flow channel 1018, for the purpose of reflecting a side fluorescence 1058, or side scatter, to a position where it can be detected. It should be appreciated that a refractive element may be used in place of, or in combination with, the reflective surface 1010. As one example, the microfluidic chip substrate may be constructed from multiple materials having different refractive indexes to achieve a desired reflection and/or refraction of light in a particular path, such as forward fluorescence or side fluorescence. In one embodiment, a reflective surface 1010*a* is associated with flow channel 1018*b* by placement substantially in parallel along the inspection region of the flow channel 1018*b* at about 45 degree angle. A side fluorescence 1058*b* is illustrated emitting from a sperm cell 1012 being excited with electromagnetic radiation 1044*a*. The side fluoresce travels until reaching the reflective surface 1010*a*, at which point the side fluorescence is redirected to be substantially parallel with the forward fluorescence signal 1052*a*. As can easily be understood, the reflective surfaces 1010 may be provided at other angles for collecting side fluorescence in manner other than in parallel with the forward fluorescence 1052.

The depicted system may include collection optics 54, like those previously described, including a large, single collection lens whereby each of forward fluorescence and side fluorescence are projected onto an image plane coincident with fiber cables is in communication with a fluorescence detector. The side fluorescence detector may be substantially identical to the forward fluorescence detector, the only difference may be in the execution of instructions stored in the analyzer 58. Alternatively, detections schemes like those depicted in FIGS. 26A-D may also be used.

A second flow channel 1018*b* is depicted producing a second forward fluorescence 1052*b* and a second side fluorescence 1058*b*, however, such an embodiment may include between 4 and 512 flow channels. In one embodiment, each set of flow channels 1018 and their associated reflective surface 1010 may be separated from other sets by a blocking element 1026 which prevents cross talk between the flow channels 1018.

Figure 25B:
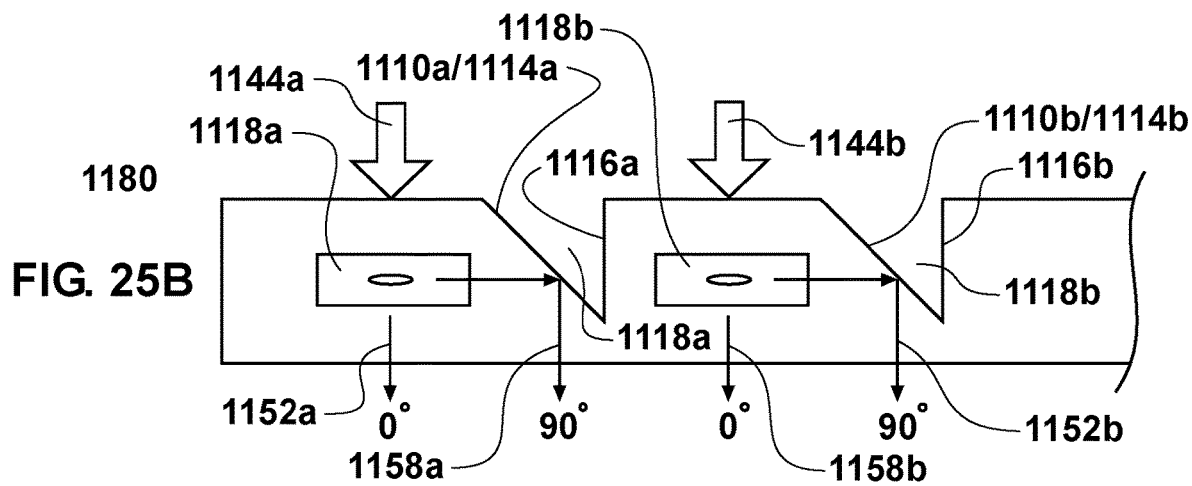

FIG. 25B illustrates a variation of the reflective surface 1110, which is formed by cutting away a portion of the substrate forming the microfluidic chip 1180. The cut away portion 1112 may have a proximal surface 1114 and a distal surface 1116 relative to the flow channel 1118. The proximal surface may comprises the reflective surface associated with the flow channel 1118, and may be capable of total internal reflection to a difference in the refractive index. Like the previous figure a blocking element may optionally be added between each set of channels and their associated reflective surface.

Turning to FIG. 25C, each flow channel 1218 is associated with a first reflective surface 1220 and a second reflective surface 1222. Each reflective surface may be provided at about 45 degrees thereby providing a −90 side fluorescence 1254 and a +90 side fluorescence 1256 in parallel with the forward fluorescence 1252. Like the previous Figure, a difference in the refractive index of the materials provides a total internal reflective surface thereby producing a forward fluorescence and two side fluorescence light paths in response to particles excited with electromagnetic radiation 1244. Such an embodiment may require a blocking element to prevent cross talk between channels.

FIG. 25D illustrates an embodiment where the internal reflective surface is provided in one or more sidewalls of the flow channel 1318 itself. The first flow channel 1318b is illustrated with a first reflective sidewall 1320a and a second reflective sidewall 1322a. However, it should be appreciated, that microfluidic chip may be fabricated so that only the first sidewall has reflective properties. Alternatively, both side walls may have reflective properties, but a detection system may be employed which only detects one of the +90 side fluorescence or −90 side fluorescence. In either event, a blocking element 1326 may be incorporated between the flow channels in order to prevent cross talk between the channels. In one embodiment, the refractive properties of various chip substrates may be altered at different locations in the chip to achieve the desired reflection and/or refraction. For example, a middle layer of the substrate, which coincides with the surfaces 1320 and 1322 may comprise a material having a different refractive index as compared to a top and bottom layer of the substrate.

Various detection systems may be employed to detect the parallel forward fluorescence and side fluorescence produced by the chips of FIGS. 25A-D. In one embodiment, a single large collection lens is incorporated for focusing each onto an image plane incident to an array of fiber optics previously described. Such an embodiment may require twice as many detectors.

Figure 26A:
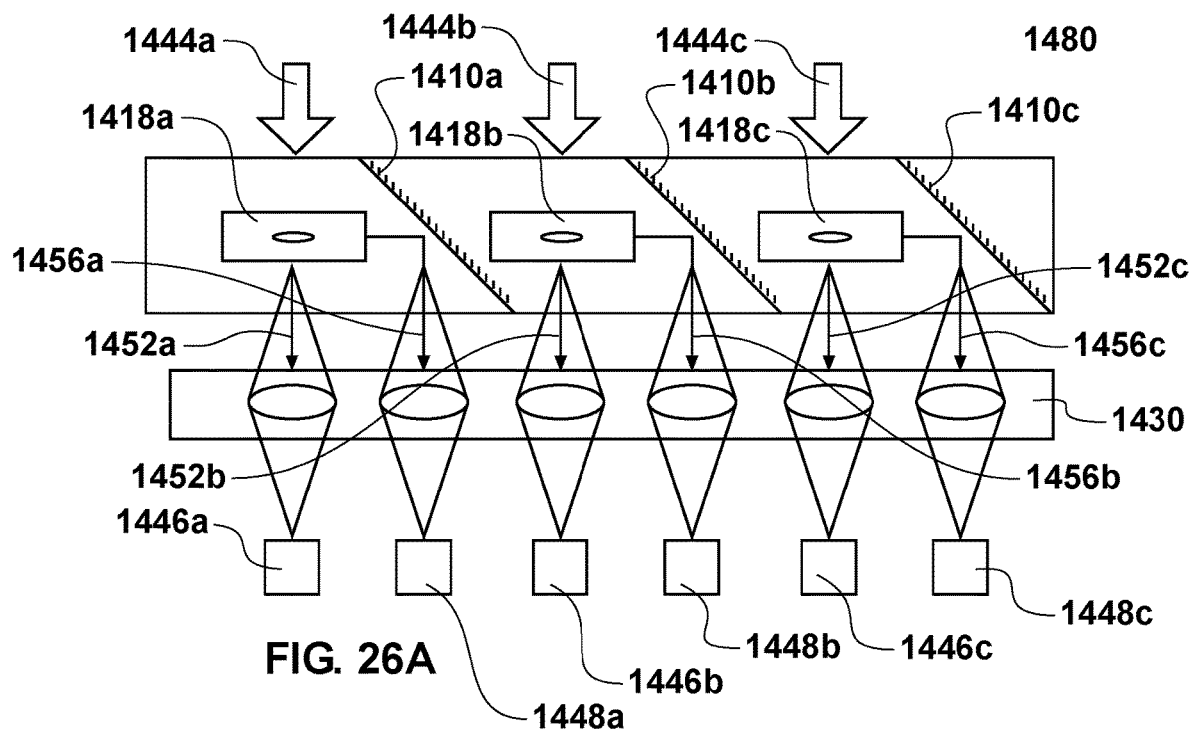
FIGS. 26A-D illustrate detection systems in accordance with certain embodiments described herein.

An alternative detection system for collecting a forward 1452 and a side fluorescence 1456 from each channel 1418 is depicted in FIG. 26A. The depicted microfluidic chip 1480 produce includes a reflective surface 1410 associated with each flow channel 1418 which provides a forward light path and a side light path in response to an excitation electromagnetic radiation 1444. An array of lenses 1430, such as an array of microlenses, may be aligned with the microfluidic chip 1480 for collecting light from each of the forward and side light paths. The array of microlenses 1430 can include a forward collection lens 1440a and a side collection lens 1442a for the first flow channel 1418b. Each forward collection lens 1440 and side collection lens 1442 may be configured to focus the collected electromagnetic radiation, whether fluorescence or scatter, onto a forward detector 1446a and a side detector 1448b, respectively. Alternatively, the array of lenses 1430 focus collected electromagnetic onto an array of fiber optic cables in communication with individual detectors.

Figure 26B:
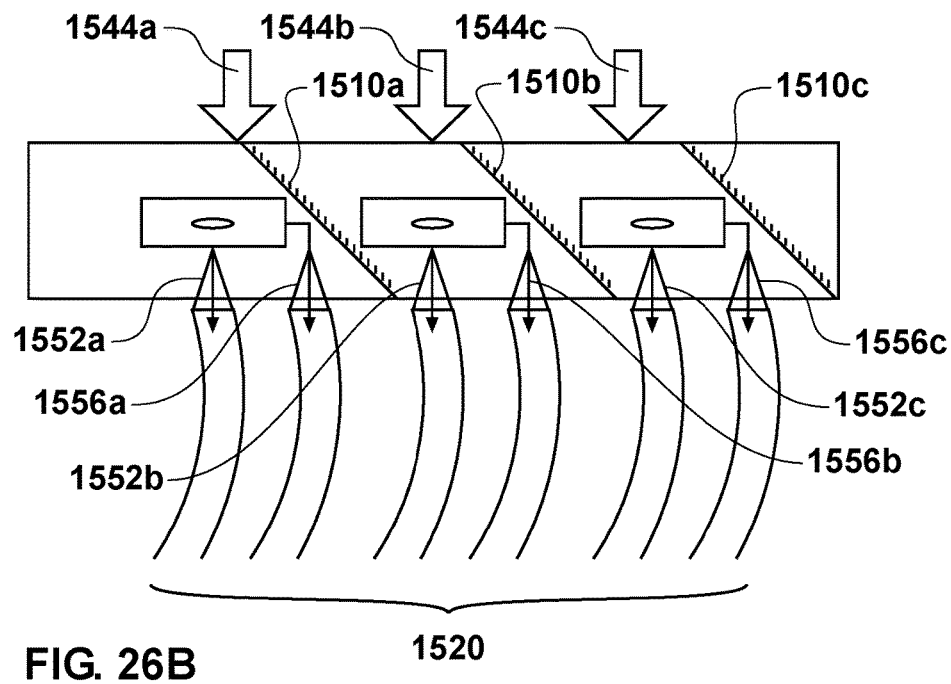
Figure 26C:
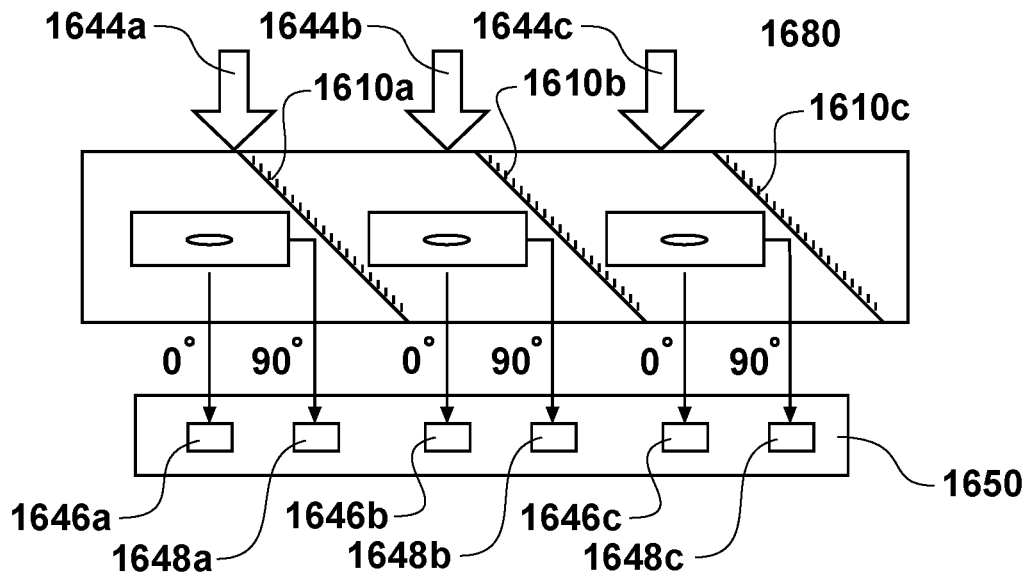

FIG. 26B illustrates an alternative embodiment including a fiber array 1520, similar to the array depicted in FIG. 23, which incorporates twice the number of fiber cables for collecting a forward fluorescence 1552 and a side fluorescence 1558 produced by an excitation electromagnetic radiation 1544 and a reflective surface 1510 associated with each flow channel 1518. Similarly, FIG. 26C provides a detector array 1650 in close proximity to the microfluidic chip 1680, whereby each flow channel 1618 has an associated reflective surface 1610, so that each excitation electromagnetic radiation 1644 may produce a forward and side fluorescence. A forward detector 1646 and a side detector 1684 are provided in the detector array 1650 for each flow channel 1618.

Figure 26D:
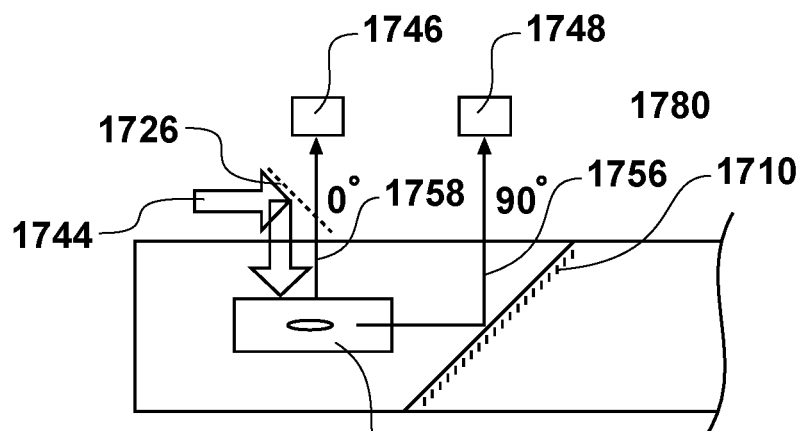

In an alternative embodiment, the detectors, or a fiber array, may be placed in an epi-illumination relationship with the excitation beam. FIG. 26D illustrates a microfluidic chip 1780, having a flow channel 1718 and an associated reflective surface 1710 angled to reflect side fluorescence, or scatter, in the direction from which the excitation beam was received where it may be received by a side detector 1748, or a fiber cable in communication with a side detector 1748. A dichroic mirror 1726 may be placed for each channel to direct an excitation beam 1744 towards the flow channel 1718, while emitted fluorescence from the cell in the back direction 1758 may pass through the dichroic mirror 1726 to a back detector 1746, or to a fiber cable in communication with a back detector 1746. The depicted example provides an internal reflective surface 1710, which may direct a side fluorescence 1756 to the side detector.

It can be readily seen, various potential solutions to the issue of sperm orientation in a plurality of parallel flow channel in a chip may add levels of complexity to the channel geometry, the collection optics, and/or to the required detector configuration.

Figure 27:
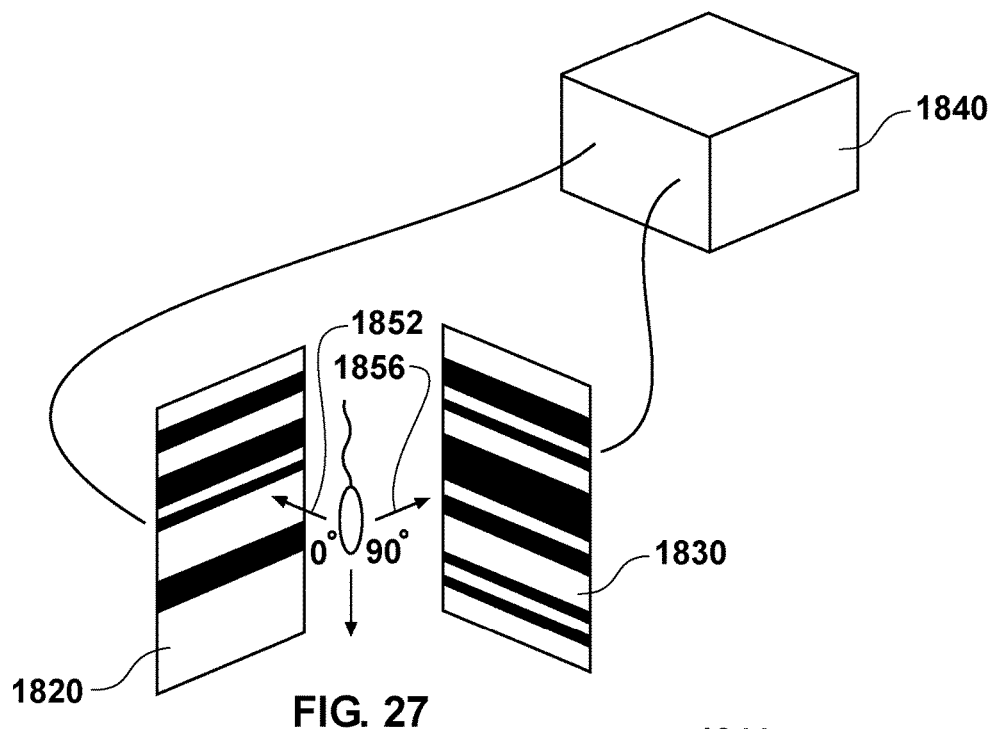
FIG. 27 illustrates a detection scheme which provides a single detector for multiple light paths in accordance with certain embodiments described herein.

Turning to FIG. 27, a potential solution exists whereby the additional detectors may be eliminated by the inclusion of masks, or a partial transmission blocking element. In particular, a first detection mask 1820 and a second detection mask 1830 may be placed in the path of the forward fluorescence 1852 and the side fluorescence 1856 respectively. Each mask may be placed in free space, may be coupled to the substrate of the chip, or may be coupled to another optical element in the path of the fluorescence. The optical path through the first detection mask 1820 and through the second detection mask 1830 may ultimately arrive at the same detector 1840, which in turn produces a waveform pulse representing information from both the forward fluorescence and the side fluorescence. The masks may be configured, for mutually exclusive transmission, such that the waveform pulse generated by the detector include segments directly attributed to the forward fluorescence and portions and segments directly attributed to the side fluorescence. Alternatively, the first detection mask 1820 and the second detection mask 1830 may overlap to some extent without unduly causing errors in measurements since an analyzer may be used to deconvolve signals.

An analyzer may deconvolve each signal from the single waveform pulse, thereby providing forward fluorescence and side fluorescence information from a single detector. Alternatively, more complex masks may be incorporated into each light path and the detector may receive signals from more than one flow channel, whereby each flow channel comprises a unique signature pattern in each associated mask.

Figure 28A:
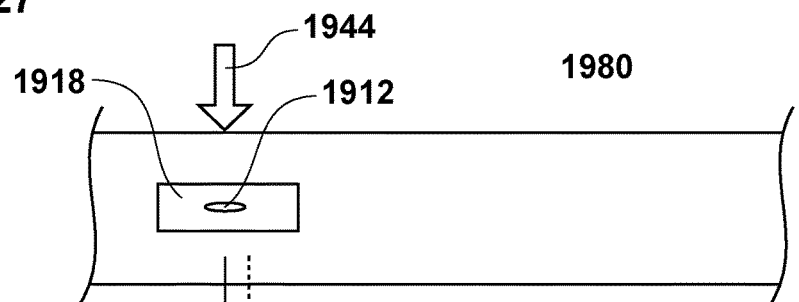
FIGS. 28A-B illustrate a detection scheme incorporating alternatives to side fluorescence detection in accordance with certain embodiments described herein.

FIG. 28A provides another embodiment of a detection scheme which may be incorporated with various other features described herein. The illustrated detection scheme eliminates the need for detecting a side fluorescence altogether and may be incorporated with each of between 4 and 512 flow channels in a microfluidic chip 1980. A sperm cell 1912 is illustrated at the inspection region of a flow channel 1918, being interrogated by a beam of electromagnetic radiation 1944. The excitation beam and a forward fluorescence carry forward in the path of the excitation beam through the microfluidic chip 1980 and encounter a dichroic mirror 1924 may reflect one of the two, since each are at a different wavelength. As one example, the electromagnetic radiation 1944 may be produced by a laser operated at a UV wavelength and may pass through the dichroic mirror 1924 and on to an absorption/extinction detector 1962. The transmitted portion of the electromagnetic radiation 1960 may be utilized for a variety of purposes. The absorption/extinction detector 1962 may be configured to effectively monitor the flow channel for the presence of cells, when a cells passes through the excitation beam 1944, the intensity of the transmitted portion 1960 that is received by the absorption/extinction detector 1962 is greatly reduced. Beyond the mere presence of a cell, the amount by which the fluorescence is extinguished may provide a quantifiable measurement for determining whether a passing sperm cell is in a desired orientation.

Figure 28B:
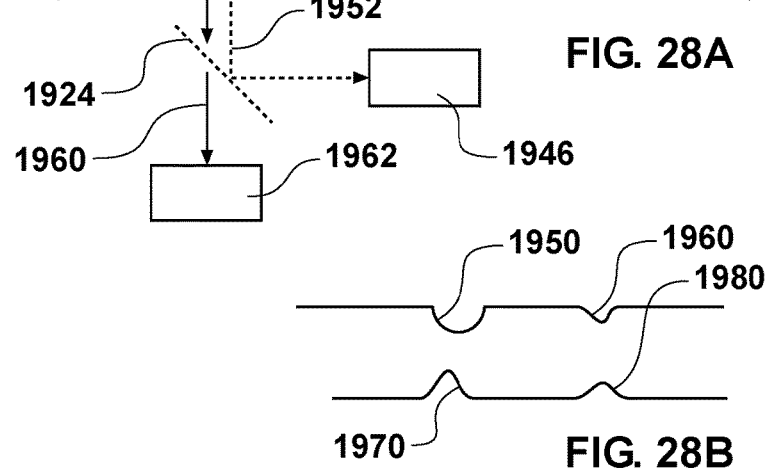

Simultaneously, a reflected forward fluorescence 1952 is incident upon a forward fluorescence detector 1946, which may be utilized to measure the DNA content of passing sperm cells 1912. FIG. 28B illustrates a representative signal produced by an extinction/absorption detector. A baseline 1940 can be seen which indicates the full power of the transmitted portion 1960 of the excitation beam is incident upon the absorption/extinction detector 1962. It should be noted the absorption/extinction detector 1962, or optics in the light path leading to the detector, may include a neutral density filter, or some other optical device for reducing the actual laser power seen by the absorption/extinction detector 1962. In either case, a baseline is established which reflects the time at which no sperm is passing through the excitation beam. A waveform pulse 1950 can be seen which represents an oriented sperm cell passing through the beam followed by a less pronounced waveform pulse representative of an unoriented sperm cell 1960.

Waveform characteristics from signals produced by the extinction detector 1962 may be calculated in order to determine which pulses characterize oriented sperm cells and which pulses characterize unoriented sperm cells. Pulse peak, pulse area, or even a pulse inner area, which may represent the some fraction of the pulse area centered around the pulse peak, may individually, or in combination provide a determination regarding sperm orientation.

FIG. 28B also illustrates a fluorescence signal from the detector 1946, the signal is illustrated having a first waveform pulse 1970 corresponding to the oriented sperm cell and a second waveform pulse 1980 corresponding to the unoriented sperm cell. When a sperm cell is determined to be oriented according to the extinction signal, the fluorescence signal may then be analyzed for pulse peak pulse area, pulse area, and/or other waveform characteristics in order to quantify the relative amount of DNA in the sperm cells for determining the presence of an X-chromosome or a Y-chromosome.

Figure 29A:
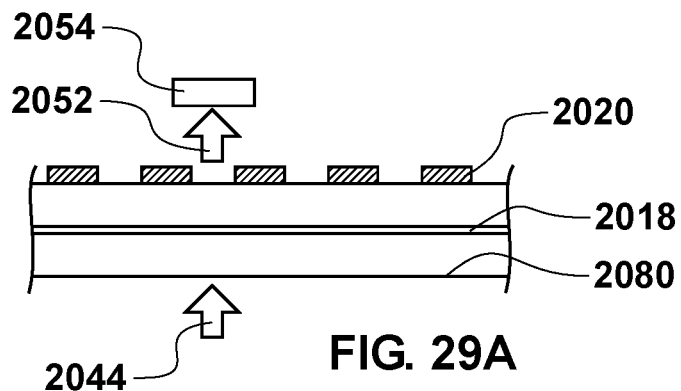
FIGS. 29A-D illustrate a detection scheme for determining sperm orientation with a forward signal in accordance with certain embodiments described herein.

FIG. 29A-D illustrates another potential configuration which eliminates both the need for side fluorescence detection and the need for a second detector. FIG. 29A generally depicts vertical sectional view a microfluidic chip 2080, having a flow channel 2018 in which an excitation beam 2044 is schematically illustrated causing sperm produce a forward fluorescence 2052 that passes through a mask 2020 and on to a detector 2054.

Figure 29B:
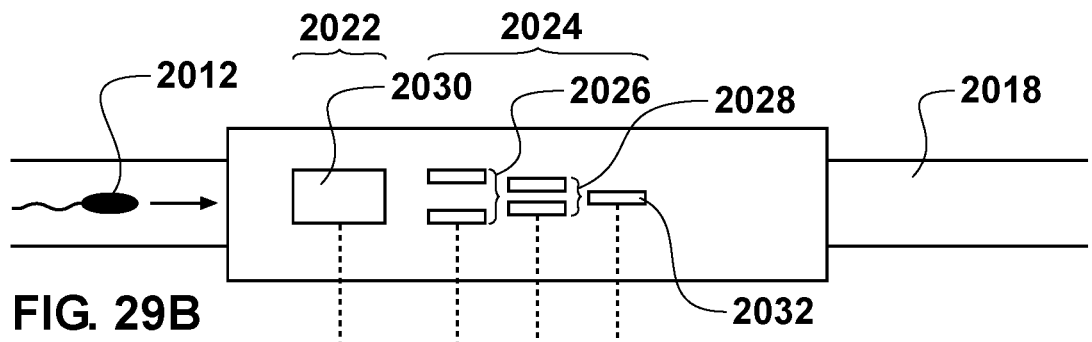
Figure 29C:
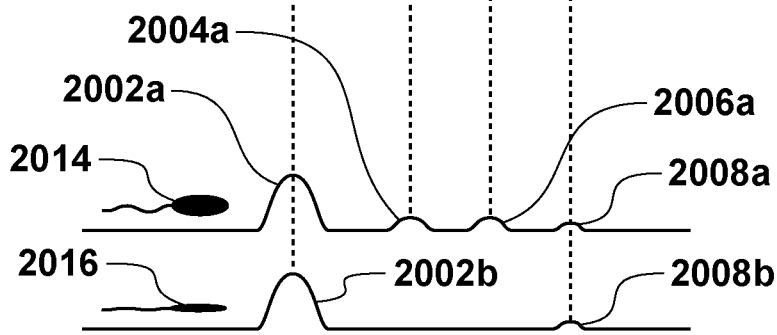

A view from above the microfluidic chip illustrated in FIG. 29B illustrates two distinct regions in the mask 2020. An oriented sperm cell 2012 is depicted traveling through the flow channel 2018 in route to the mask 2020. The signals produced by each distinct mask region pass through to the same detector 2054 and may provide a series of waveform pulses. The signal generated by the detector 2054 at this window may be seen in FIG. 29B for the instance of oriented sperm 2014 and unoriented sperm 2016.

The first mask region 2022 may be the DNA content measuring portion of the mask 2020 and may comprise a single aperture 2030 that is at least as wide as the sperm being measured, and at least as long as the sperm head. A peak height and peak area may be determined from the first waveform pulse 2002A in order to differentiate X-chromosome bearing sperm from Y-chromosome bearing sperm, whereas the first waveform pulse 2002B of an unoriented sperm 2016, may be excluded from classification according to a sort logic.

The second mask region 2024 may comprise multiple openings. In one embodiment, several spaced pairs of opening may be sequentially located along the flow path 2018. Each pair of openings may have a different transverse position, although there may also be some overlap. In one embodiment, the spaced opening may be 1 to 10 microns wide, although smaller and larger widths may also be used. The first spaced pair of openings 2026 are illustrated as the furthest apart. Consequently, oriented sperm 2014 will tend to fluoresce well enough through both openings to produce a second waveform pulse 2004A, while unoriented sperm 2016 may produce a pulse of half the intensity, but likely will not produce any waveform pulse.

A second pair of openings 2028 is illustrated slightly further downstream and spaced more closely together. Oriented sperm 2014 will fluorescence through both openings in the mask to produce a third waveform pulse 2006A. Depending on the degree of misorientation, an unoriented sperm 2016 may produce some fluorescence at this portion of the mask, but the illustrative example provides an edge to the detector, and still no waveform pulse is generated. A final opening 2032 in the second region 2024 is illustrated in the center of the flow path 2018. Again, oriented sperm 2014 may produce a fourth waveform pulse 2008A. Even unoriented sperm 2016 having an edge facing the mask may produce a fourth waveform pulse 2008B.

The detector is provided in communication with an analyzer which may decipher the presence or absence of the second, third and fourth waveform pulses in order to determine whether a sperm cell was oriented when it passed through the inspection region. In a digital system, once a determination of orientation is made, the pulse area and/or the pulse peak of the first pulse waveform can be evaluated and a determination regarding sex characteristics can be made.

Figure 29D:
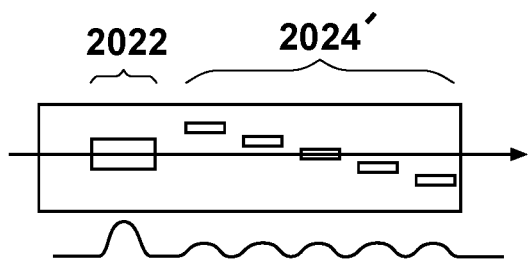

FIG. 29D provides an alternative arrangement for the second mask region 2024', in the form of slits progressively moving in transverse pattern along the flow path. It should be appreciated any number of other similar configurations may be incorporated into the second mask region 2024'. In an unpaired configuration, the number of waveform pulses, may provide an indication of whether a sperm is oriented and how unoriented it may be. It could be understood any number of patterns may be employed, as long as there are some differences in the transverse position of the apertures, or slits.

As can be understood from the foregoing, features described for focusing a core stream, or aligning sperm in a flow channel, may be combined with various features for orienting sperm, as well as with various features for detecting sperm orientation, and even with other features for focusing a core stream. Similarly, one or more of the described orientation features may be employed in a single flow channel for the purpose of orienting sperm. The basic concepts of the present invention may be embodied in a variety of ways and in a variety of combinations. The invention involves numerous and varied embodiments of sex sorting sperm including, but not limited to, the best mode of the invention. As such, the particular embodiments or elements of the invention disclosed by the description or shown in the figures or tables accompanying this application are not intended to be limiting, but rather illustrative of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A sperm sorting system comprising:
   a microfluidic chip comprising a generally planar substrate having a flow channel in which sample fluid is contacted and surrounded by sheath fluid;
   a sheath inlet for introducing the sheath fluid into the flow channel;
   a sample inlet for introducing a sample fluid containing sperm cells that is injected into a flow of sheath fluid in the flow channel;
   a fluid focusing region in the flow channel located downstream of the injection of sample fluid into sheath fluid in the flow channel, wherein the fluid focusing region comprises a vertical fluid focusing geometry having a gradually decreasing channel height;
   a sperm orienting region located downstream of the fluid focusing region in the flow channel and sized to further focus the sample fluid and to orient sperm cells in the plane of the substrate, wherein the sperm orienting region comprises a vertically tapering region that at least partially overlaps a laterally tapering region and wherein the sperm orienting region is between 200 microns and 5000 microns in length;
   an inspection region located downstream of the sperm orienting region for illuminating the sperm cells with electromagnetic radiation from an electromagnetic radiation source; and
   a re-expansion region located downstream of the inspection region.

2. The system of claim 1, wherein the electromagnetic radiation source comprises a 355 nm quasi continuous wave laser.

3. The system of claim 1, wherein the microfluidic chip comprises multiple flow channels.

4. The system of claim 3, further comprising a beam splitting device configured to divide electromagnetic radiation from said electromagnetic radiation source and direct a portion of said electromagnetic radiation to the inspection region of the flow channels.

5. The system of claim 1, wherein the sperm orienting region further comprises one or more of the following channel features: a ramp, and a step.

6. The system of claim 1, wherein the fluid focusing region further comprises a tapering lateral focusing region.

7. The system of claim 1, wherein the vertical taper of the vertically tapering region and the lateral taper of the laterally tapering region occur along the flow channel at different rates.

8. The system of claim 1, further comprising a flow channel transition from a square cross section to a rectangular cross section.

9. The system of claim 1, wherein the sperm orienting region comprises a first rectangular cross section that transitions to a second rectangular cross section along the flow channel.

10. The system of claim 1, wherein the flow channel comprises a first width and a first height at the sample inlet.

11. The system of claim 10, wherein the flow channel comprises a second width and a second height at a first transition point.

12. The system of claim 11, wherein the width of the flow channel is reduced between the sample inlet and the first transition point.

13. The system of claim 12, wherein the flow channel comprises a third width and a third height at a second transition point.

14. A microfluidic chip for sorting sperm comprising:
a generally planar substrate;
a flow channel having a height and a width formed in the substrate in which sample fluid is contacted and surrounded by sheath fluid;
a fluid focusing region positioned at a location in the flow channel where the sample fluid is surrounded by sheath fluid when in operation, wherein the fluid focusing region comprises one or more of a lateral fluid focusing region and a vertical fluid focusing region; and
a sperm orienting region downstream of the fluid focusing region, wherein the sperm orienting region is sized to further focus the sample fluid and to orient sperm cells in the plane of the substrate and comprises a region of gradually decreasing flow channel height and a region of decreasing flow channel width.

15. The microfluidic chip of claim 14, further comprising multiple flow channels.

16. The microfluidic chip of claim 14, wherein the fluid focusing region comprises a vertical fluid focusing region.

17. The microfluidic chip of claim 14, wherein the lateral fluid focusing region comprises a tapering lateral fluid focusing region.

18. The microfluidic chip of claim 14, wherein the decrease in flow channel height along the flow channel comprises a decrease to about 50 microns.

19. The microfluidic chip of claim 14, wherein the decrease in flow channel width along the flow channel comprises a decrease from at least 1000 microns to about 200 microns.

20. The microfluidic chip of claim 14, wherein the region of decreasing flow channel height in the sperm orienting region overlaps at least partially with the region of decreasing flow channel width.

21. The microfluidic chip of claim 14, wherein the decrease in flow channel height and the decrease in flow channel width occur along the flow channel at different rates.

22. The microfluidic chip of claim 14, wherein the sperm orienting region comprises a first elliptical cross section that transitions to a second elliptical cross section.

23. The microfluidic chip of claim 14, wherein the decrease in flow channel height and the decrease in flow channel width comprises a flow channel transition from a square cross section to a rectangular cross section.

24. The microfluidic chip of claim 14, wherein the flow channel comprises a first width and a first height at the sample inlet.

25. The microfluidic chip of claim 24, wherein the flow channel comprises a second width and a second height at a first transition point.

26. The microfluidic chip of claim 25, wherein the width of the at least one flow channel is reduced between the sample inlet and the first transition point.

27. The microfluidic chip of claim 26, wherein the flow channel comprises a third width and a third height at a second transition point.

* * * * *